(12) United States Patent
LaPlante et al.

(10) Patent No.: US 11,185,118 B2
(45) Date of Patent: Nov. 30, 2021

(54) SENSOR CONNECTION ASSEMBLY FOR INTEGRATION WITH GARMENT

(71) Applicant: Murata Vios, Inc., Woodbury, MN (US)

(72) Inventors: Brandon J. LaPlante, Minneapolis, MN (US); Scott Mazar, Woodbury, MN (US)

(73) Assignee: MURATA VIOS, INC., Woodbury, MN (US)

( * ) Notice: Subject to any disclaimer, the term of this patent is extended or adjusted under 35 U.S.C. 154(b) by 643 days.

(21) Appl. No.: 15/880,111

(22) Filed: Jan. 25, 2018

(65) Prior Publication Data

US 2018/0213859 A1    Aug. 2, 2018

Related U.S. Application Data

(60) Provisional application No. 62/450,400, filed on Jan. 25, 2017.

(51) Int. Cl.
*A61B 5/00* (2006.01)
*A41D 13/12* (2006.01)
(Continued)

(52) U.S. Cl.
CPC .......... *A41D 13/1236* (2013.01); *A61B 5/282* (2021.01); *A61B 5/303* (2021.01);
(Continued)

(58) Field of Classification Search
CPC ............ A41D 13/1236; A41D 13/1281; A41D 1/002; A61B 5/0402; A61B 5/04085;
(Continued)

(56) References Cited

U.S. PATENT DOCUMENTS 7,206,630 B1 * 4/2007 Tarler .................. A61B 5/0006
600/509
8,818,478 B2    8/2014 Scheffler et al.
(Continued)

FOREIGN PATENT DOCUMENTS

EP          2042093         4/2009

OTHER PUBLICATIONS

International Search Report and Written Opinion in International Application No. PCT/US2018/015296, dated Apr. 26, 2018, 20 pages.

*Primary Examiner* — Joseph A Stoklosa
*Assistant Examiner* — Rachel A. Vierra
(74) *Attorney, Agent, or Firm* — Keating & Bennett, LLP

(57) ABSTRACT

A patient worn sensor assembly for detecting, recording, and communicating patient vital signs can be integrated into a garment to be worn by the patient. A lead assembly can be integrated into a garment to connect electrodes in contact with the skin of a patient to a sensor assembly that collects vital sign information from the electrodes. The lead assembly can be multi-layered and can include, for example, two outer anti-static satin fabric layers as top and bottom layers, muslin fabric insulator layers adjacent to the anti-static satin fabric layers, shield layers that include muslin with silver fabric adjacent to the insulator layers, and an inner layer of (Continued)

fabric with conductive thread (or alternatively conductive thread not integrated with other fabrics, or a layer that is substantially composed of conductive thread).

18 Claims, 21 Drawing Sheets

(51) Int. Cl.
    *A61B 5/282*     (2021.01)
    *A61B 5/30*     (2021.01)
    *A61B 5/318*     (2021.01)

(52) U.S. Cl.
    CPC ............ *A61B 5/318* (2021.01); *A61B 5/6804* (2013.01); *A61B 5/6805* (2013.01); *A61B 5/6823* (2013.01); *A61B 2562/182* (2013.01); *A61B 2562/222* (2013.01)

(58) Field of Classification Search
    CPC ... A61B 5/6804; A61B 5/6805; A61B 5/6823; A61B 2562/182; A61B 2562/222; A51B 5/0402; A51B 5/04286; A51B 5/6804; A51B 5/6805; A51B 5/6823
    See application file for complete search history.

(56) References Cited

U.S. PATENT DOCUMENTS

| | | | |
|---|---|---|---|
| 8,954,129 B1 | 2/2015 | Schlegel et al. | |
| 2005/0034485 A1* | 2/2005 | Klefstad-Sillonville | A41D 13/1281 66/171 |
| 2006/0076810 A1* | 4/2006 | Nichols | A47C 7/386 297/220 |
| 2009/0088652 A1* | 4/2009 | Tremblay | A61B 5/6814 600/388 |
| 2010/0234715 A1* | 9/2010 | Shin | A61B 5/0537 600/388 |
| 2011/0073353 A1* | 3/2011 | Lee | D03D 15/00 174/254 |
| 2015/0094556 A1* | 4/2015 | Geva | A61B 5/0416 600/382 |
| 2015/0126844 A1 | 5/2015 | Yang et al. | |
| 2015/0223716 A1 | 8/2015 | Korkala et al. | |
| 2015/0359485 A1* | 12/2015 | Berg | A61B 5/04 600/388 |
| 2016/0228060 A1 | 8/2016 | Mazar et al. | |
| 2017/0027469 A1 | 2/2017 | Amir et al. | |
| 2017/0143977 A1 | 5/2017 | Kaib et al. | |
| 2017/0278585 A1* | 9/2017 | Almer | B32B 5/08 |

\* cited by examiner

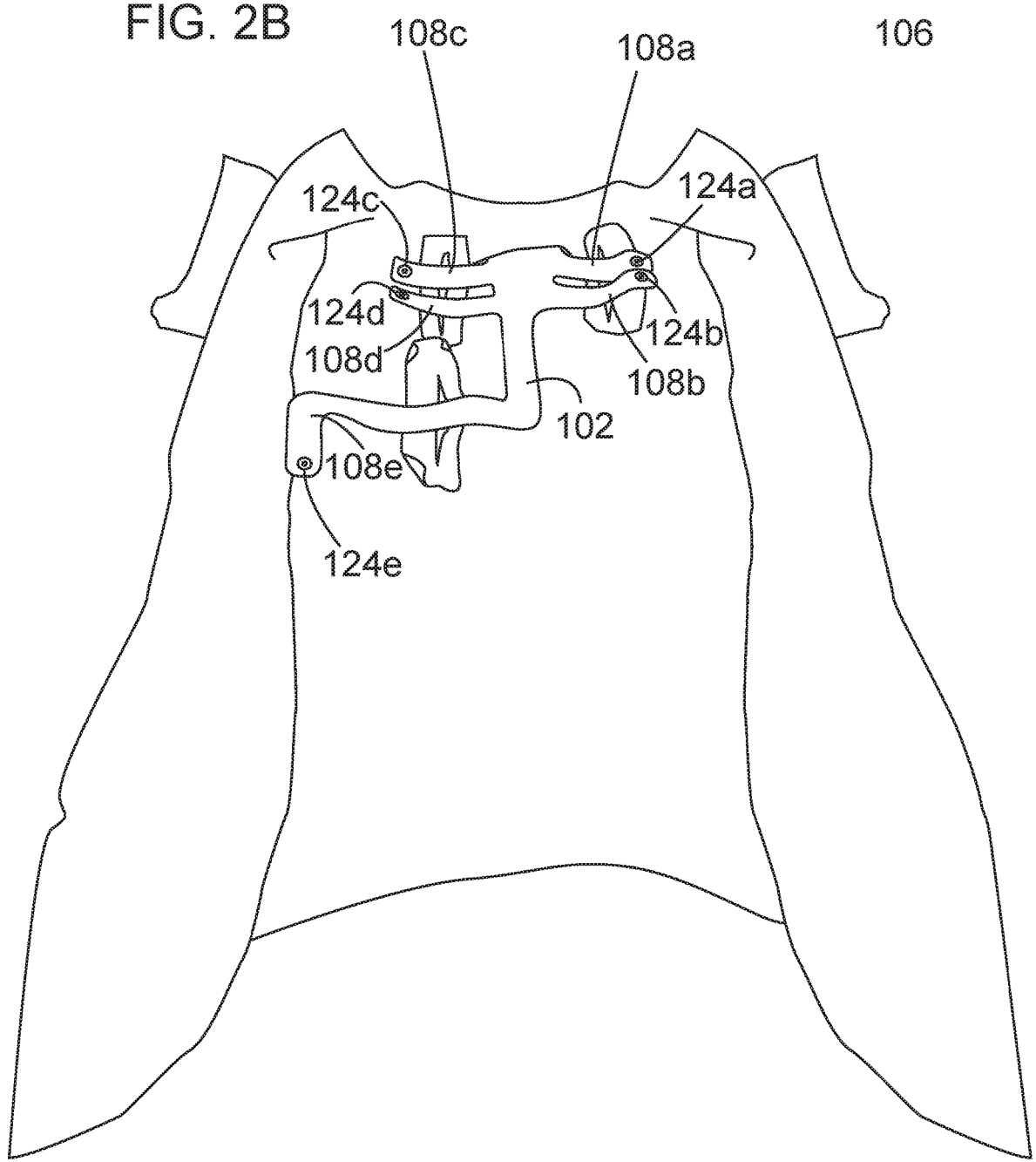

SENSOR CONNECTION ASSEMBLY FOR INTEGRATION WITH GARMENT

CROSS-REFERENCE TO RELATED APPLICATION(S)

This application claims priority to U.S. Provisional Application No. 62/450,400, filed on Jan. 25, 2017. The disclosure of this prior application is considered part of and is incorporated by reference in the disclosure of this application.

FIELD OF TECHNOLOGY

The present disclosure is directed toward patient monitoring devices and systems that include portable, wearable components that can be affixed to or integrated with garments.

BACKGROUND

Many different types of patient monitoring systems require a direct electrical interface to the skin of a patient. In some applications, the direct electrical interface to the patient's skin is for sensing electrical information present at that skin location, while in other applications, the direct electrical interface is for injecting an electrical current signal at that skin location. One example of a device with a skin electrical interface is a patient-worn sensor device that, among other capabilities, may collect patient electrocardiogram ("ECG") information sensed at the skin of the patient and wirelessly transmit data indicative of the collected ECG information for receipt by another system such as a hospital, clinic or home-based monitoring system. In this wearable ECG sensor device example, the device typically includes firstly an adhesive electrode assembly with multiple individual electrodes wherein the assembly is adapted to be attached to the patient's skin, and secondly a sensor assembly that includes all of the sensing, processing and communication electronics and a power supply for a self-contained sensor-transmitter device. In this case, the electrode assembly provides the direct electrical interface and adhesion to the patient's skin as well as a platform to which the sensor assembly connects and is supported.

Another class of skin electrode assemblies are adapted to be connected by an electrical lead (or in other words, a long wire) to a separate monitoring system, and are intended to be used with the patient "tethered" to the monitoring system. In this electrode assembly example, the patient-worn assembly typically includes an electrode assembly with one or more electrodes adapted to be adhered to the patient's skin and an associated connector assembly with an associated number of contacts to the electrodes of the electrode assembly. The connector assembly is adapted such that a monitoring system lead may be connected to it to provide an electrical connection between the one or more electrodes of the electrode assembly and the sensing and processing circuitry of the separate monitoring system.

SUMMARY

A patient worn sensor assembly for detecting, recording, and communicating patient vital signs can be integrated into a garment to be worn by the patient. A lead assembly can be integrated into a garment to connect electrodes in contact with the skin of a patient to a sensor assembly that collects vital sign information from the electrodes. The lead assembly can be multi-layered and can include, for example, two outer anti-static satin fabric layers as top and bottom layers, muslin fabric insulator layers adjacent to the anti-static satin fabric layers, shield layers that include muslin with silver fabric adjacent to the insulator layers, and an inner layer of fabric with conductive thread (or alternatively conductive thread not integrated with other fabrics, or a layer that is substantially composed of conductive thread). The conductive thread can connect to electrodes at various points and to a sensor assembly that processes vital sign information sensed at the electrodes (e.g., for the purpose of transmitting the information to an external computing device). In some implementations, portions of the conductive thread layer can terminate in contact with snap connectors for engaging electrodes of adherent electrode pads and for connecting the conductive thread to the sensor assembly. In some implementations, the adherent electrode pads can be disposable. The disposable adherent electrode pads can be periodically removed and replaced with a fresh adherent electrode pad while allowing many of the components of the patient worn sensor (such as the multi-layered lead assembly) to be continually reused. In some implementations, portions of the conductive thread layer can terminate in contact with a connector (e.g., a wired connector terminating in an adapter) for engaging a corresponding connector of the sensor assembly.

In general, in one aspect, a multi-layered lead assembly for use with a garment can include a first anti-static layer; a first insulator layer positioned adjacent to the first anti-static layer; a first shield layer positioned adjacent to the first insulator layer; a center layer having fabric interwoven with conductive thread, such that the conductive thread forms a plurality of electrical traces extending within the center layer, the center layer positioned adjacent to the first shield layer; a second shield layer positioned adjacent to the center layer; a second insulator layer positioned adjacent to the second shield layer; and a second anti-static layer positioned adjacent to the second insulator layer; wherein the first anti-static layer, first insulator layer, first shield layer, center layer, second shield layer, second insulator layer, and second anti-static layer as sewn together to form the multi-layered lead assembly.

In various embodiments, the multi-layered lead assembly can optionally include various features such as the following. The first and second shield layers can be partially or completely made of muslin fabric integrated with a silver fabric. The silver fabric of the first and second shield layers can extend to a point such that it does not extend to the edges of the first and second shield layers. The conductive thread of the center layer can have silver woven through it. The center layer can include four distinct electrical traces formed from the conductive thread such that each of the four electrical traces terminates at a first end configured to electrically couple with a respective electrode for contacting skin of a patient and wherein each of the four electrical traces terminates at a second end configured to electrically couple with a sensor assembly. The first end of each electrical trace can be configured to electrically couple with the respective electrode via a female snap connector. Each respective electrode can include a portion of conductive rubber and the first end of each electrical trace is configured to electrically couple with the respective portion of conductive rubber.

The second end of each electrical trace can be configured to electrically couple with the sensor assembly via a male snap connector. The second end of each electrical trace can form at least a portion of an adapter configured to electrically couple with the sensor assembly. The first and second anti-static layers can be made entirely or partially of satin fabric. The first and second insulator layers can be made entirely or partially of muslin fabric. The conductive thread of the center layer can include silver.

The multi-layered lead assembly can further include a first extending portion having a first electrical connector for connecting a first electrical trace of the center layer to a first electrode such that the first electrical trace and the first electrode form a left arm type electrode, wherein the first electrical trace terminates at an end opposite the first electrode at a first connector configured to engage a sensor assembly; a second extending portion having a second electrical connector for connecting a second electrical trace of the center layer to a second electrode such that the second electrical trace and the second electrode form a right arm type electrode, wherein the second electrical trace terminates at an end opposite the second electrode at a second connector configured to engage the sensor assembly; and a third extending portion having a third electrical connector for connecting a third electrical trace of the center layer to a third electrode such that the third electrical trace and the third electrode form a left leg type electrode, wherein the third electrical trace terminates at an end opposite the third electrode at a third connector configured to engage the sensor assembly.

The multi-layered lead assembly can further include a fourth extending portion having a fourth electrical connector for connecting a fourth electrical trace of the center layer to a fourth electrode such that the fourth electrical trace and the fourth electrode form a current injection electrode for injecting current as part of a bio-impedance measurement process, wherein the fourth electrical trace terminates at an end opposite the fourth electrode at a fourth connector configured to engage the sensor assembly.

The third extending portion of the multi-layered lead-assembly can be generally L shaped. The first, second, and third connectors can be male snap connectors. The first, second, and third connectors can make up at least a part of an adapter having a wire portion and a connector portion, the connector portion configured to engage a corresponding connector portion of the sensor assembly.

BRIEF DESCRIPTION OF THE DRAWINGS

FIGS. 2A-2B show a multi-layered lead assembly affixed to a garment.

Like reference numerals refer to like elements.

DETAILED DESCRIPTION

Figure 1A:
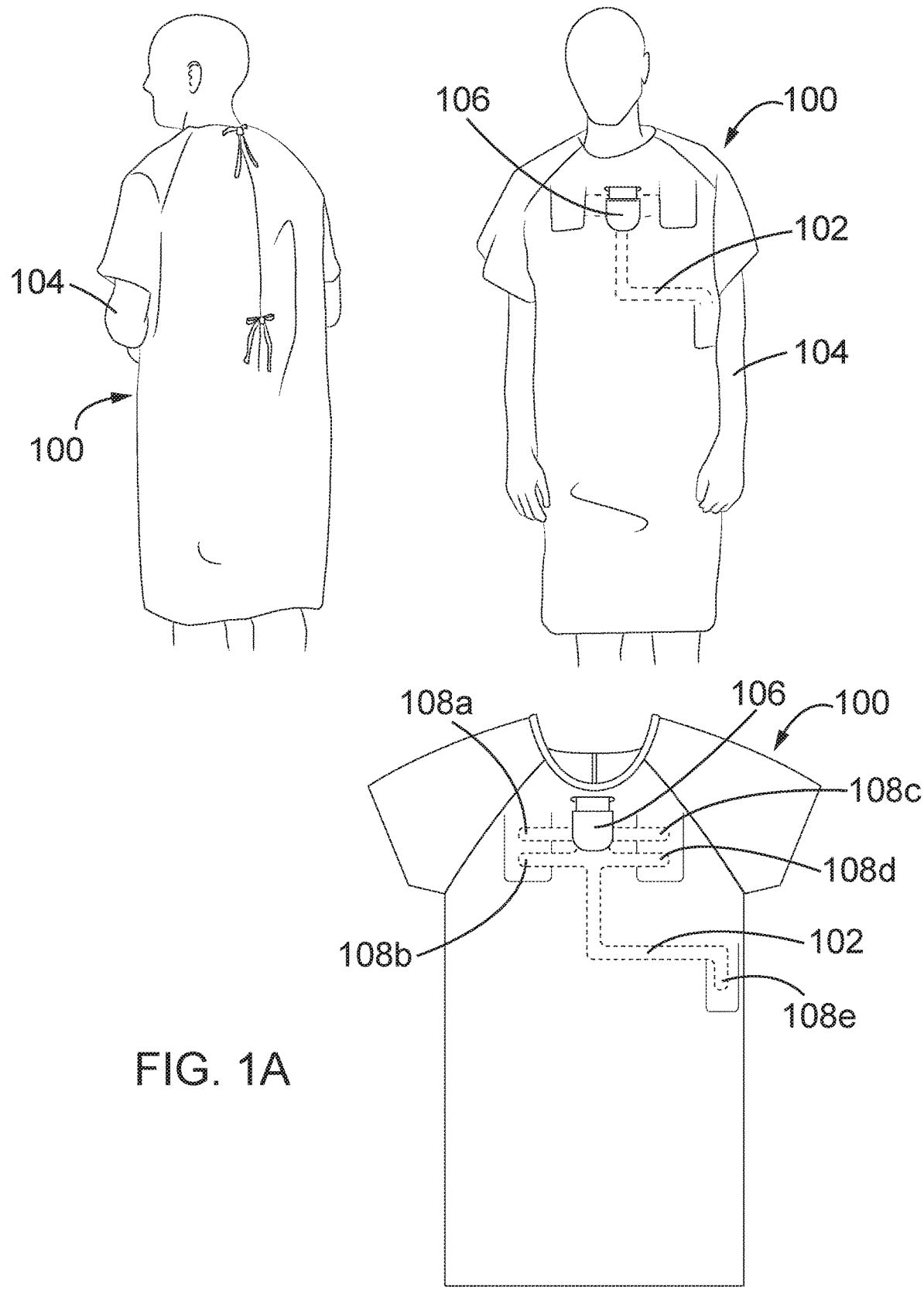
FIGS. 1A-1F show example embodiments of a garment that includes a multi-layered lead assembly configured to contact a sensor assembly and various electrodes.

FIG. 1A shows an example embodiment of a patient worn garment 100 (e.g., a medical gown such as the type generally worn in a hospital setting) having integrated therein (or alternatively, affixed thereto) a multi-layered lead assembly 102 configured to operatively connect various electrodes in contact with the skin of a patient 104 with a sensor assembly (not shown) that can be carried by or affixed to the garment (such as in a pocket 106 configured to hold the sensor as shown in FIG. 1A). The electrodes can be, for example, ECG electrodes having gels that can contact the patient 104's skin and affix to the patient 104's skin to sense vital signs. Alternatively, the electrodes can be conductive material such as conductive rubber that can be, for example, integrated as part of the garment 100 and/or the multi-layered lead assembly 102. The electrodes can be either adhesive or non-adhesive. Extending portions of the multi-layered lead assembly 102 can be positioned within the garment 100 such that when the garment 100 is worn by a patient, the ends of extending portions 108a-e of the multi-layered lead assembly 102 are positioned so as to collect various vital sign measurements of the patient 104. For example, some or all of the extending portions 108a-e can be positioned such that they can connect to electrodes that are positioned on the patient 104's skin to serve as left arm, right arm, left leg, and right leg (ground) type electrodes.

For example, in some implementations, the extending portion 108a connects (e.g., releasably or permanently) with an ECG electrode gel, conductive rubber, or other type of electrode to form a "right arm" electrode. The extending portion 108b can connect (e.g., releasably or permanently) with an ECG electrode gel, conductive rubber, or other type of electrode to serve as an electrode that is used in a bio-impedance measurement. For example, the extending portion 108b in conjunction with an electrode in contact with the patient 104's skin can serve as a current injection electrode for use in a bio-impedance measurement. For example, the extending portion 108b in conjunction with an electrode in contact with the patient 104's skin can serve as a current injection electrode for a 4-point bio-impedance measurement in which a known value of current is injected into a patient and a pair of electrodes are used to measure the induced voltage, which can be used along with the known current value to calculate the bio-impedance.

Continuing with FIG. 1A. The extending portion 108c can connect (e.g., releasably or permanently) with an ECG electrode gel, conductive rubber, or other type of electrode form a "left arm" electrode. The extending portion 108d can connect (e.g., releasably or permanently) with an ECG electrode gel, conductive rubber, or other type of electrode form a "right leg" (ground) electrode. The extending portion 108e can connect (e.g., releasably or permanently) with an ECG electrode gel, conductive rubber, or other type of electrode form a "left leg" electrode.

Figures 1, 1B:
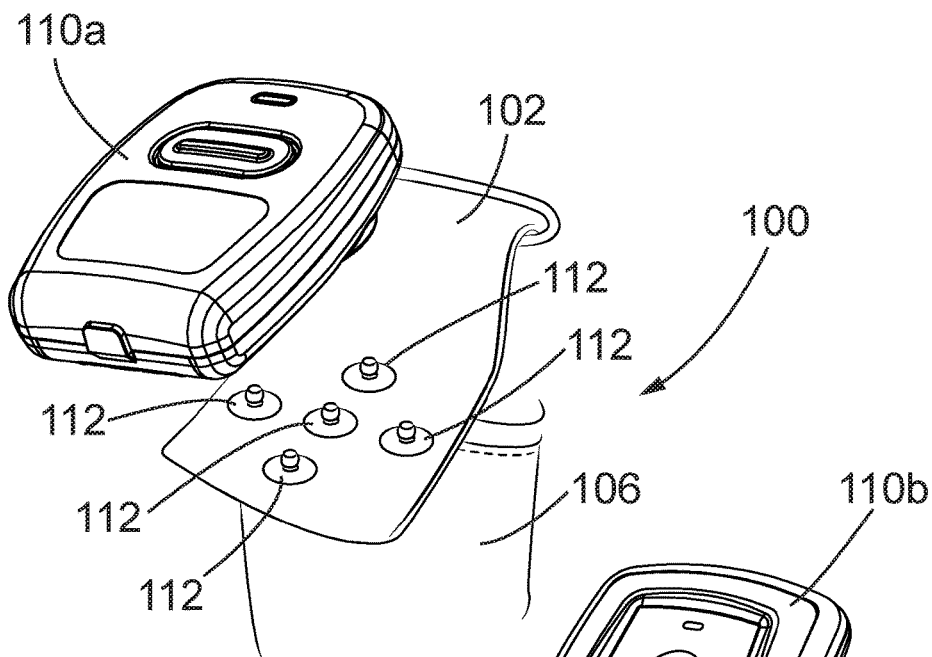

FIGS. 1B-1 to 1B-3 show close up detail of portions of the garment 100 depicted in FIG. 1A along with various embodiments of a sensor assembly and sensor assembly connector. FIG. 1B-1 shows close up detail of portions of the garment 100 depicted in FIG. 1A including a sensor assembly 110a that can connect to one or more snap contacts 112 (five snap contacts 112 in the example shown) of a portion of the multi-layered lead assembly 102. The sensor assembly can be, for example, of the type described in U.S. patent application Ser. No. 15/019,431 filed on Feb. 9, 2016 (published as U.S. Patent Publication No. US-2016-0228060-A1 on Aug. 11, 2016), the entire disclosure of which is hereby incorporated by reference. The sensor assembly 110a includes female snaps for releasably coupling to the male snap contacts 112 of the multi-layered lead assembly 102 of the garment 100. Each of the snap contacts 112 depicted in FIG. 1B-1 is electrically coupled to a respective one of the extending portions 108a-e of the multi-layered lead assembly 102. As described above, each of the extending portions 108a-e is coupled to an electrode in contact with the skin of the patient wearing the garment 100 and therefore the snap contacts 112 are in electrical communication with the skin of the patient and transfer biometric signals detected at the patient's skin to the sensor assembly 110a where the biometric signals can be received, processed, stored, and/or transmitted to other electronic/computing devices. In this way, the multi-layered lead assembly 102 (including extending portions 108a-e), the electrodes in contact with the patient's skin, and the snap contacts 112 form a circuit that provides bioelectric signals collected from the patient to the sensor assembly 110a. The pocket 106 of the garment 100 is configured/shaped to support and partially conceal the sensor assembly 110a. The pocket 106 can be configured to securely hold the sensor assembly 110a close to the patient to minimize jostling or movement of the sensor assembly 110a thereby minimizing noise in the signals received from the multi-layered lead assembly 102. In some implementations, the weight of the sensor assembly 110a is partially supported by the snap contacts 112.

Figures 1, 1B, 2:
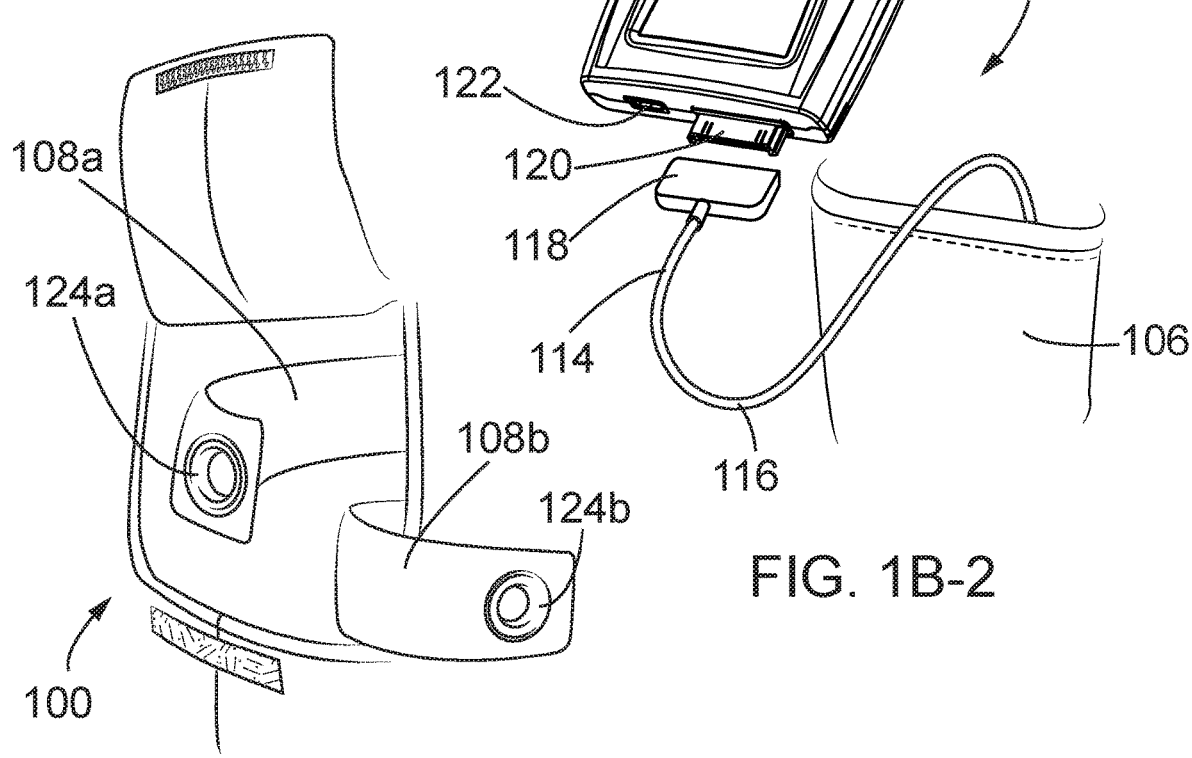
Figures 1, 1B, 2, 3:
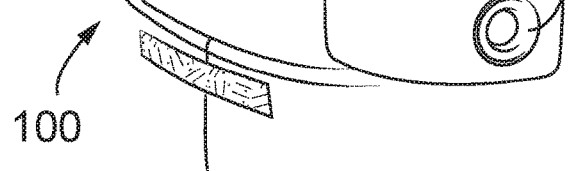

FIG. 1B-2 shows close up detail of another implementation of the garment 100 depicted in FIG. 1A including an alternative embodiment sensor assembly 110b that is configured to connect to an adapter 114 of the of the multi-layered lead assembly 102. The adapter 114, for example, includes a wire portion 116 that includes leads in electrical communication with each of the extending portions 108a-e of the multi-layered lead assembly 102. The adapter 114 further includes a connector end 118 that is configured to releasably couple with a corresponding connector 120 of the sensor assembly 110b. The connector 120 and connector end 118 can be, for example, corresponding USB connectors, firewire connectors, lightening connectors, 30-pin connectors (such as, for example, a JAE 30 pin DD1 series connector), a custom proprietary connector, or any suitable connector that would be known to a person having ordinary skill in the art.

The adapter 114 includes leads that are in electrical communication with the skin of the patient wearing the garment 100 via the extending portions 108a-e of the multi-layered lead assembly 102. For example, as previously explained, each of the extending portions 108a-e is coupled to an electrode in contact with the skin of the patient wearing the garment 100 and therefore the leads of the adapter 114 are in electrical communication with the skin of the patient and transfer biometric signals detected at the patient's skin to the sensor assembly 110b where the biometric signals can be received, processed, stored, and/or transmitted to other electronic/computing devices. In this way, the multi-layered lead assembly 102 (including extending portions 108a-e), the electrodes in contact with the patient's skin, and the adapter 114 (including the wire portion 116 having leads in communication with the extending portions 108a-e and the connector end 118) form a circuit that provides bioelectric signals collected from the patient to the sensor assembly 110b.

The sensor assembly 110b can further include a communications port 122 that is configured to releasably couple with a communications wire for purposes of transferring information (e.g., patient biometric signal information, vital sign information, etc.) to an external computing device. The communications port 122 can also receive a power adapter for charging internal batteries of the sensor assembly 110b from an external power source.

The pocket 106 of the garment 100 is configured/shaped to support and partially conceal the sensor assembly 110b. The pocket 106 can be configured to securely hold the sensor assembly 110b close to the patient to minimize jostling or movement of the sensor assembly 110b thereby minimizing noise in the signals received from the multi-layered lead assembly 102.

FIG. 1B-3 shows ends of extending portions 108a and 108b of multi-layered lead assembly 102 emerging from an opening in the garment 100. In the implementation shown, the extending portions 108a and 108b terminate in female snap connectors 124a and 124b respectively. The female snap connectors 124a-b shown in FIG. 1B-3 can serve to contact electrodes affixed to the patient's skin so that signals from the electrodes can be conveyed to the sensor assembly 110a or sensor assembly 110b (referred to collectively as sensor assembly 110 going forward). The other extending portions 108c-e of the multi-layered lead assembly 102 can include similar female snap connectors for electrically coupling to electrode gels in contact with the skin of a patient. In some implementations, the electrical contacts 124 (snap contacts) of the multi-layered lead assembly 102 are made of stainless steel. This allows the multi-layered lead assembly 102 to be washing machine washable. As discussed above, in some implementations, rather than, or in addition to, the female snap connectors 124, one or more of the extending portions 108a-e of the multi-layered lead assembly 102 include conductive material, such as conductive rubber. In some implementations, in place of the electrical contacts, some or all of the extending portions of the multi-layered lead assembly can include conductive material (such as conductive rubber) configured to engage a patient's skin directly.

FIGS. 1C-1F show an embodiment of the garment 100 from FIGS. 1A-1B in which the pocket 106 that holds the sensor assembly 110, and the electrical contacts (e.g., snap contacts 112 or adapter 114) for connecting the sensor assembly 110 to the multi-layered lead assembly 102 are located in proximity to the center of a patient's chest. Such a location for the multi-layered lead assembly 102 can improve stability of the multi-layered lead assembly 102 and minimize unwanted movement or jostling of the multi-layered lead assembly 102, thereby reducing signal noise for biometric signals collected from the patient. In alternative embodiments, the pocket 106 can be located at other portions of the garment 100, such as along the patient's side or near the patient's waist. The pocket 106 can include an elastic portion 126 that can help to secure the sensor assembly 110 within the pocket 106 when the sensor assembly 110 is operatively connected to the multi-layered lead assembly 102. In some alternative embodiments, the sensor assembly 110 can be supported by a means other than the pocket 102, such as by a hook-and-loop connector, zippers, straps, or other types of connectors.

Figure 1C:
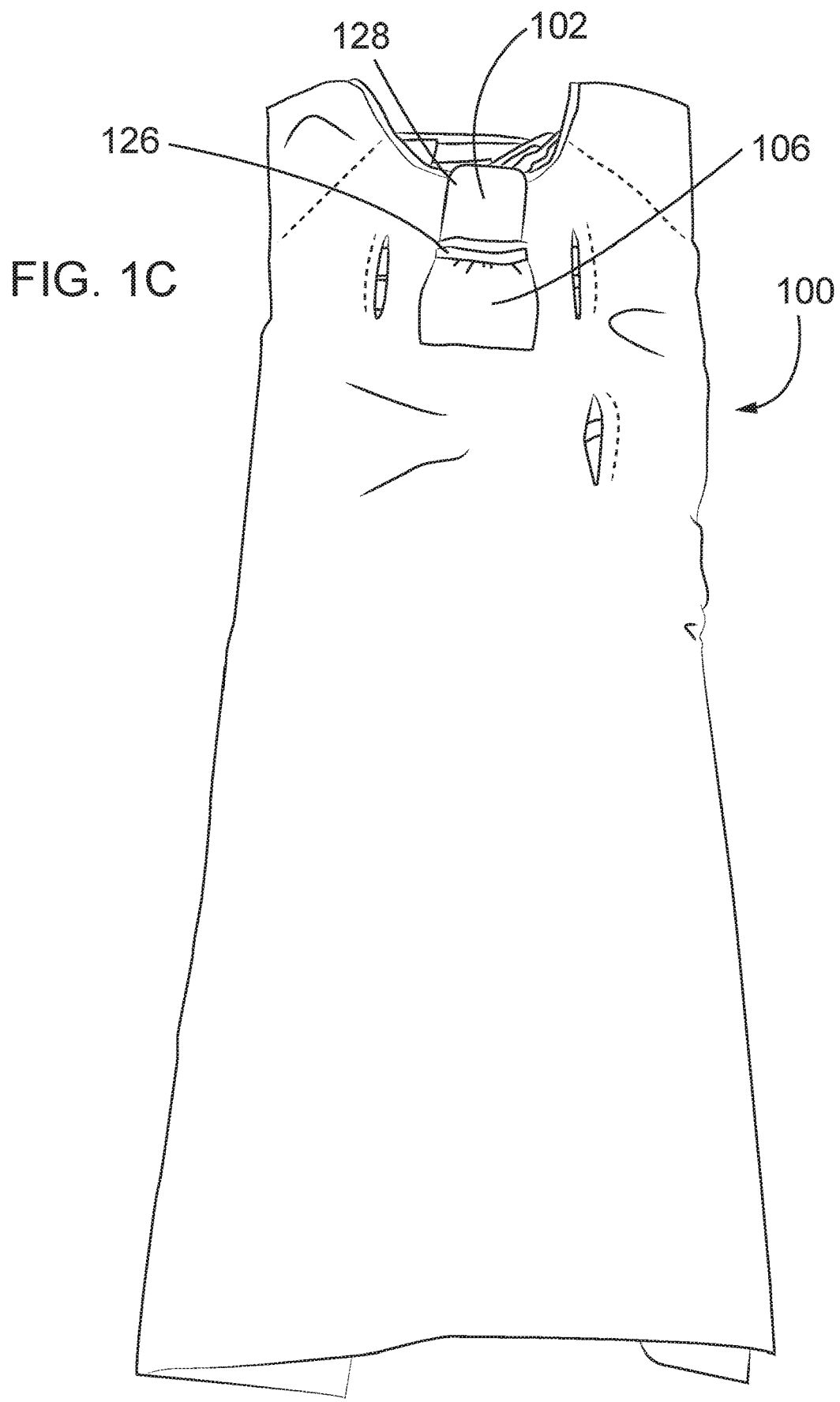
Figure 1D:
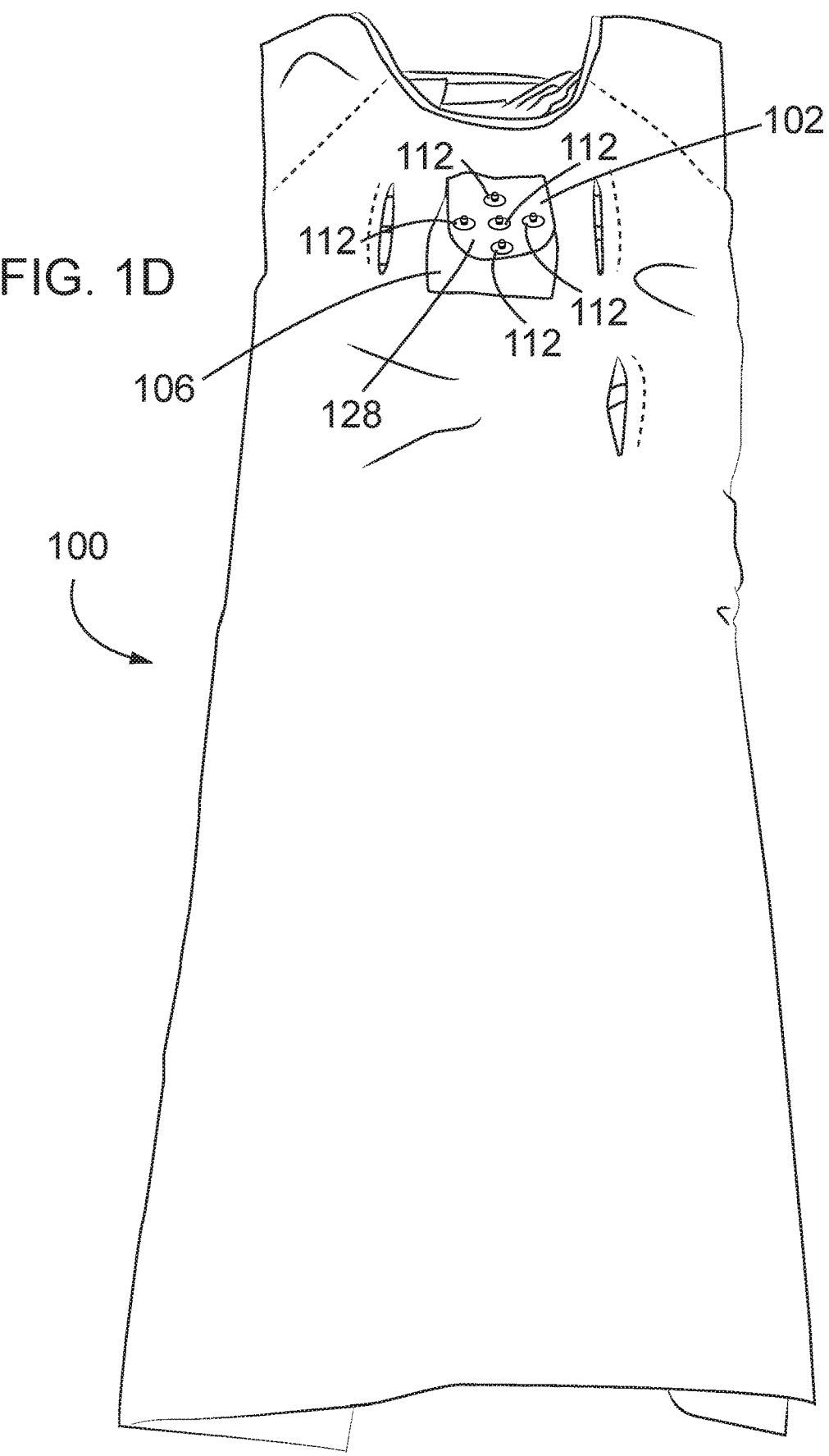
Figure 1E:
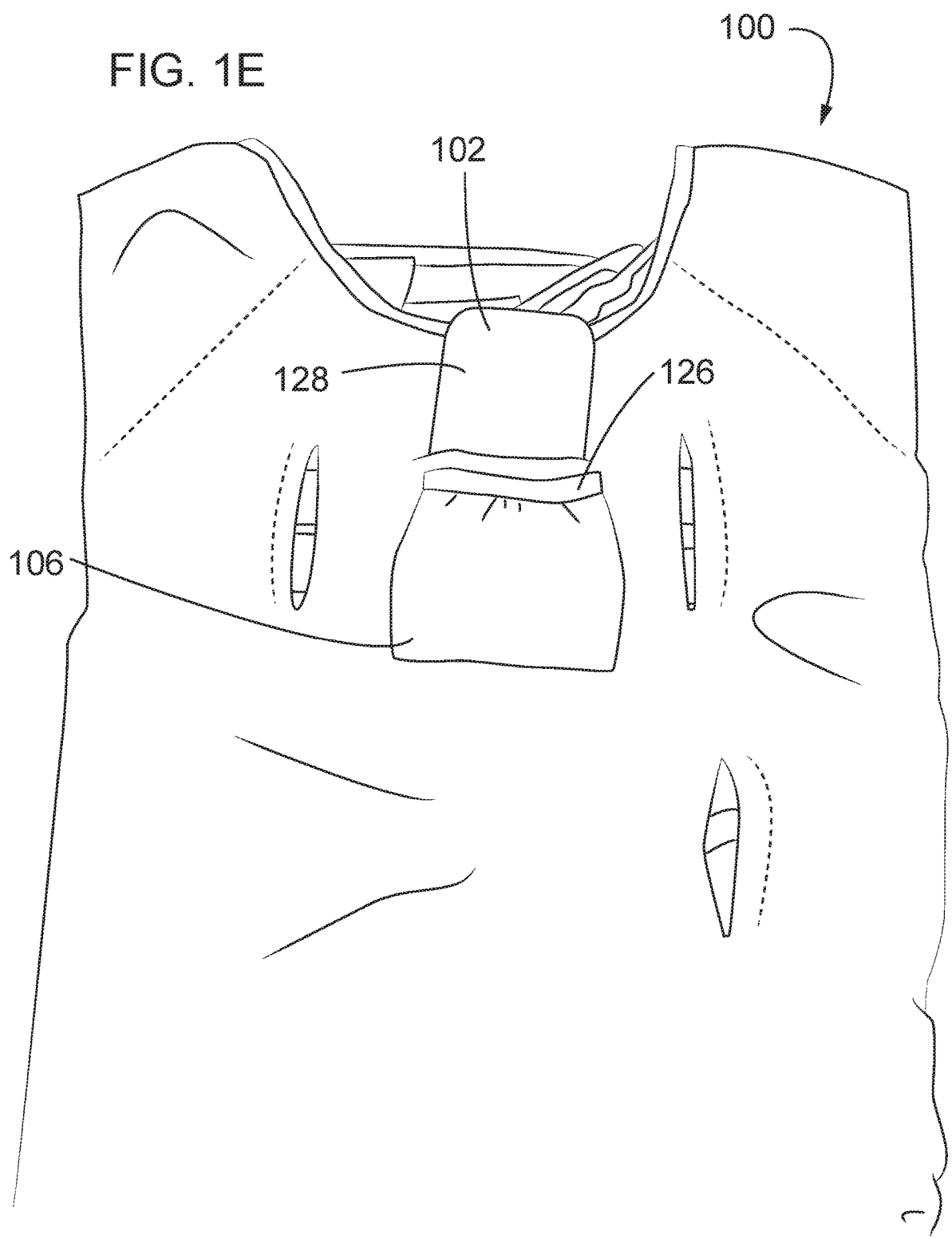
Figure 1F:
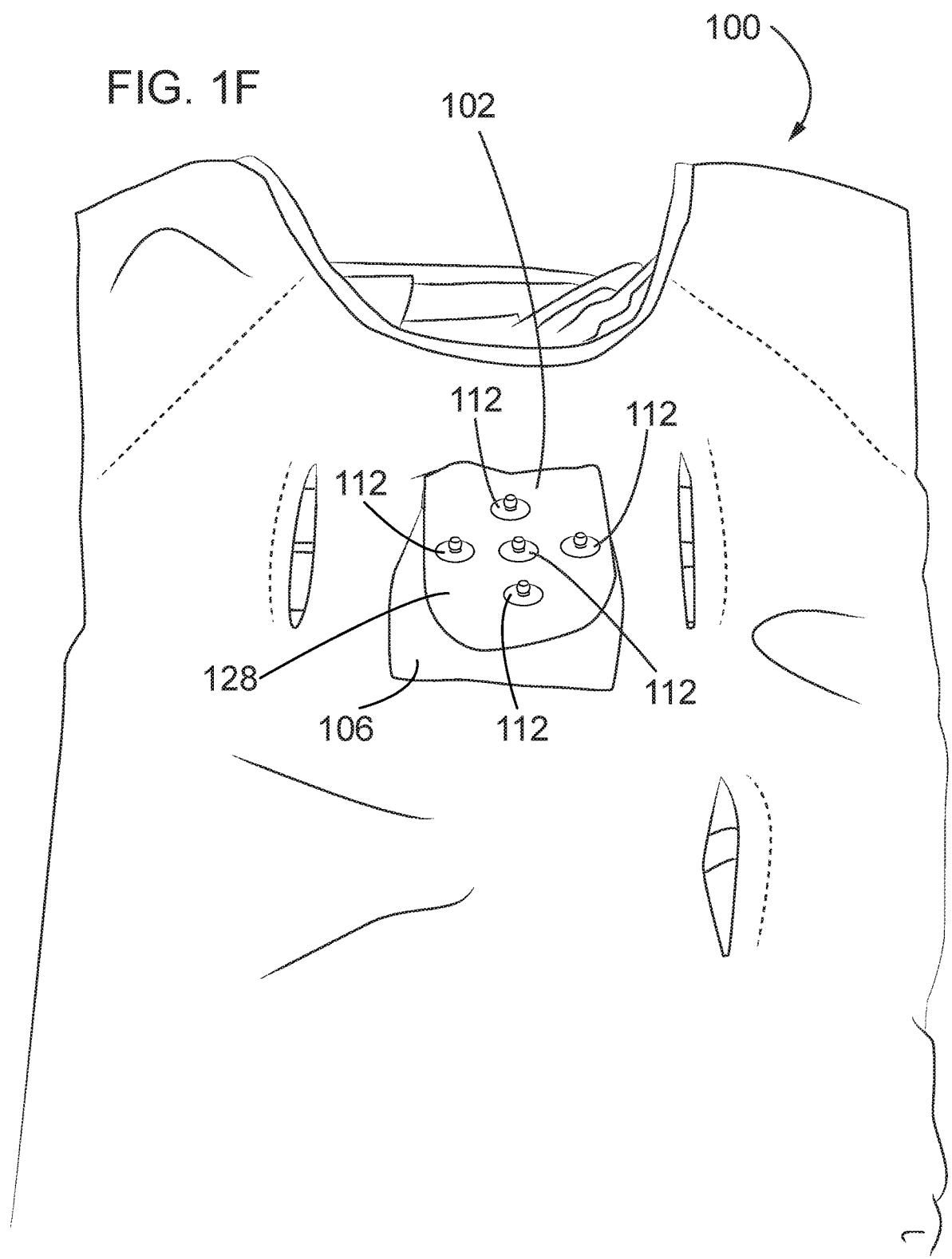

An end portion 128 of the multi-layered lead assembly 102 that includes the electrical contacts for engaging the sensor assembly (e.g., the snap contacts 112 or the adapter 114) extends out from the garment 100 near the pocket 106 for holding the sensor assembly 102. FIGS. 1C-1F depict the garment 100 with the sensor assembly 110 detached. FIGS. 1C and 1E show this end portion 128 of the multi-layered lead assembly 102 flipped up to better show the pocket 106 for holding the sensor assembly 110 while FIGS. 1D and 1F show this end portion 128 of the multi-layered lead assembly 102 flipped down in an operative position such that the snap contacts 112 for engaging the sensor assembly 110a are shown. In alternative implementations, the end portion 128 is in operative contact with the adapter 114 which connects to the sensor assembly 110b. In some implementations that include the adapter 114, the end portion 128 of the multi-layered lead assembly 102 is shorter such that the end portion 128 does not extend from the garment 100, or the end portion 128 is absent completely such that the adapter 114 extends from an opening in the garment 100 to engage the sensor assembly 110b. Returning to the example depicted in FIGS. 1C-1F, when the sensor assembly 110 is affixed to the end portion 128 of the multi-layered lead assembly (e.g. by snapping female electrical contacts of the sensor assembly 110a to the male electrical contacts 112 shown in FIGS. 1D and 1F, or by coupling the connector 120 of the sensor assembly 110b and connector end 118 of the adapter 114) the sensor assembly 110 can be supported and concealed by the pocket 106.

Figure 2A:
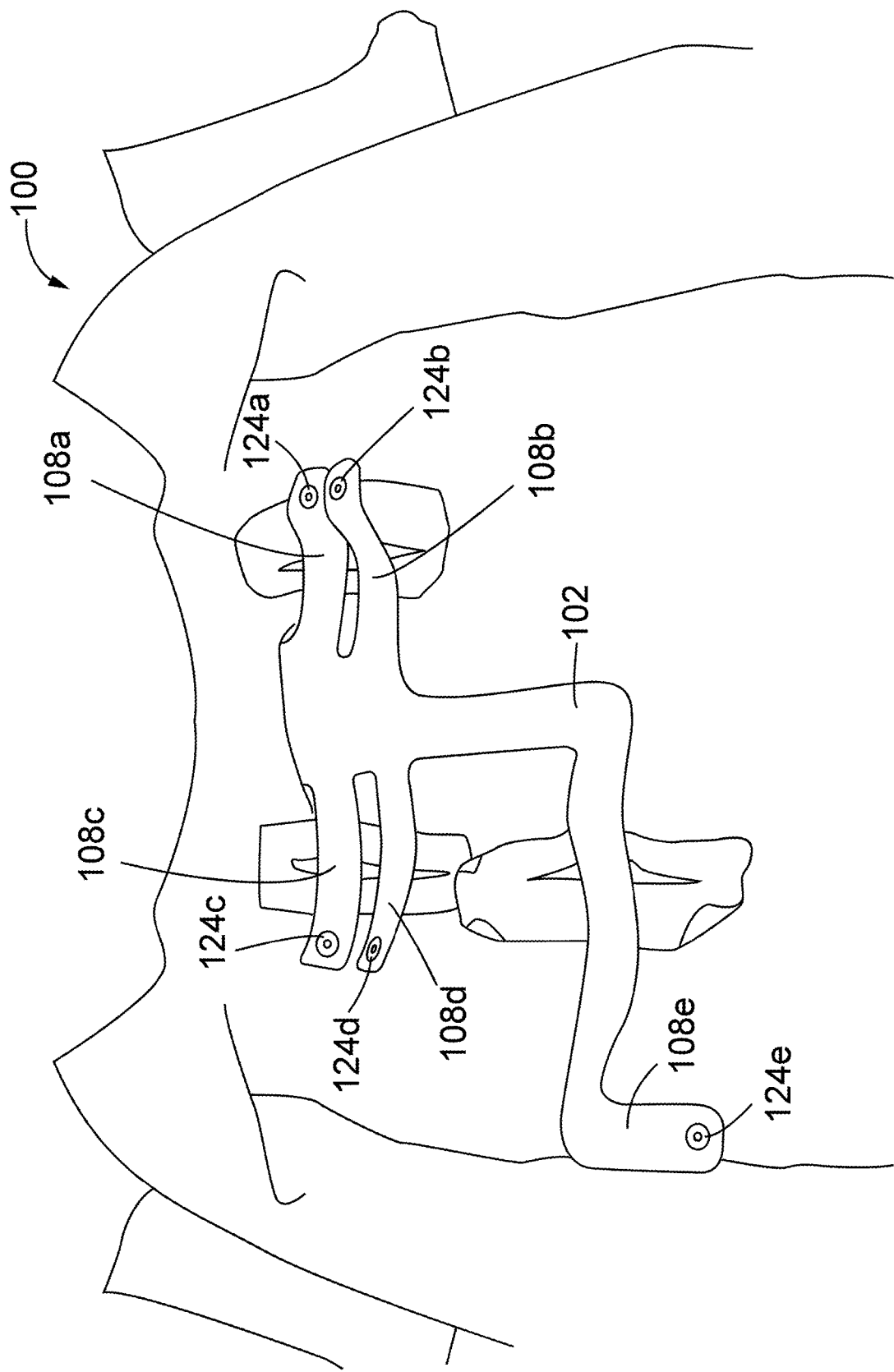

FIGS. 2A-2B show an example multi-layered lead assembly 102 affixed to the inside of the garment 100 shown in FIGS. 1C-1F. In this example, the multi-layered lead assembly 102 includes five extending portions 108a-e, each terminating in a female electrical contact 124a-e (respectively) configured to engage male electrical contacts of electrodes affixed to a patient's skin (e.g., so called "wet" electrodes that include gels for affixing to a patient's skin, sometimes referred to as electrode "dots"). In some embodiments, the electrodes can comprise conductive material, such as conductive rubber. In some embodiments, in place of the electrical contacts 124a-e, some or all of the extending portions 108a-e of the multi-layered lead assembly 102 can include conductive material (such as conductive rubber) configured to engage a patient's skin directly. This conductive material can be positioned, for example, at or near the ends of the extending portions 108a-e.

Some or all of the five extending portions 108a-e of the multi-layered lead assembly 102 depicted in FIGS. 2A-2B can engage electrodes (or alternatively include electrodes) for sensing various vital signs of a patient. For example, the upper left extending portion 108c can connect to an electrode that serves as a "left arm" electrode, the next extending portion 108d positioned immediately below the upper left extending portion 108c can connect to an electrode that serves as a reference electrode, more commonly with limb leads, the "right leg" (ground) electrode. The upper right extending portion 108a can connect to an electrode that serves as a "right arm" electrode, the next extending portion 108b immediately below the upper right extending portion 108a can connect to an electrode that is used in a bio-impedance measurement (e.g. can be used in a bio-impedance measurement along with the right leg electrode in electrical communication with extending portion 108d).

For example, the right extending portion 108b along with an electrode in contact with the patient's skin can serve as a current injection point (e.g., current injection electrode) that is driven by a sensor assembly in electrical communication with electrical leads extending throughout the multi-layered lead assembly 102. For example, the extending portion 108b and a corresponding electrode can serve as a current injector for a bi-impedance measurement and the extending portion 108d and a corresponding electrode (which form the "right leg electrode") can serve as the collection point or ground. The extending portion 108b and corresponding electrode can inject a known current of a sufficiently safe/low current into the patient which is collected at the ground electrode formed by the extending portion 108d and its corresponding electrode. The voltage of this current can be measured by the right and left arm electrodes formed by the extending portions 108a and 108b and their respective skin contacting electrodes. The known voltage and measured current can then be used to calculate bio-impedance using known techniques. This method of determining bio-impedance is sometimes referred to as a 4-point bio-impedance measurement. In some implementations, the injected current is an alternating-current ("A/C") current. In some implementations, the injected A/C current is sufficiently high that it is out of band of the relevant ECG measurements such that the injected current does not interfere with ECG measurements taken at the various electrodes. For example, the injected current can have a frequency of 32 KHz. This can allow the same electrodes (formed by extending portions 108a and 108b in contact with respective electrodes) to be used to measure both bio-impedance (via a voltage measurement) and ECG measurements.

The spatial placement of the female electrical contacts 124a-d at the ends of extending portions 108a-d can improve the bio-impedance measurement. Specifically, the vector formed between the locations of the electrodes affixed to female electrical contacts 124b and 124d (the current injecting and collecting electrodes, respectively, which form the drive vector) is substantially parallel to the vector formed between the locations of the electrodes affixed to female electrical contacts 124a and 124c (the voltage measuring electrodes). This parallel configuration ensures a better signal for the voltage measuring electrodes affixed to the female electrical contacts 124a and 124c, thereby improving the voltage measurement and the overall bio-impedance calculation. This relative positioning of the electrodes also reduces artifact of bio-impedance measurement in the ECG reading, especially in cases when an alternating current is used.

In some implementations, the functions of the electrode formed by the extending portion 108d and its corresponding electrode and the extending portion 108b and its corresponding electrode can be reversed. Specifically, the extending portion 108d and its corresponding electrode can function as the current injecting electrode and the extending portion 108b and its corresponding electrode can function as the ground/current collector electrode.

Continuing with FIG. 2A, the extending portion 108e in the lower left can connect to an electrode that serves as a "left leg" electrode. This configuration of electrodes can be used to collect various vital sign measurements from a patient wearing the garment 100. For example, the left arm and right arm electrodes can be used as a Lead (or vector) I in an ECG measurement while the right arm and left leg electrodes are used as a Lead (or vector) II in an ECG measurement. In some implementations, the right leg electrode serves as a ground.

The extending portion 108e of the multi-layered lead assembly 102 is positioned in the lower left of FIG. 2A and has an "L" shape to reduce unwanted stresses on an electrode in contact with this multi-layered lead assembly 102. The "L" shape is an improvement over straight line extensions in that it reduces compressing forces that might compress portions of an electrode gel coupled to snap connector 124e of extending portion 108e (or an electrode embedded in or otherwise affixed to 108e, such as a conductive rubber electrode) and reduce signal quality or lead to incorrect signals. These compressing forces can occur due to, for example, pulling on the extending portion 108e as the patient moves. The "L" shape allows the electrode to rotate about the snap connector 124e of the extending portion 108e without pulling on the electrode and causing compression of the electrode gel as the patient moves.

Turning to FIGS. 2C-2I, these figures show various layers of an example multi-layered lead assembly 102.

Figure 2C:
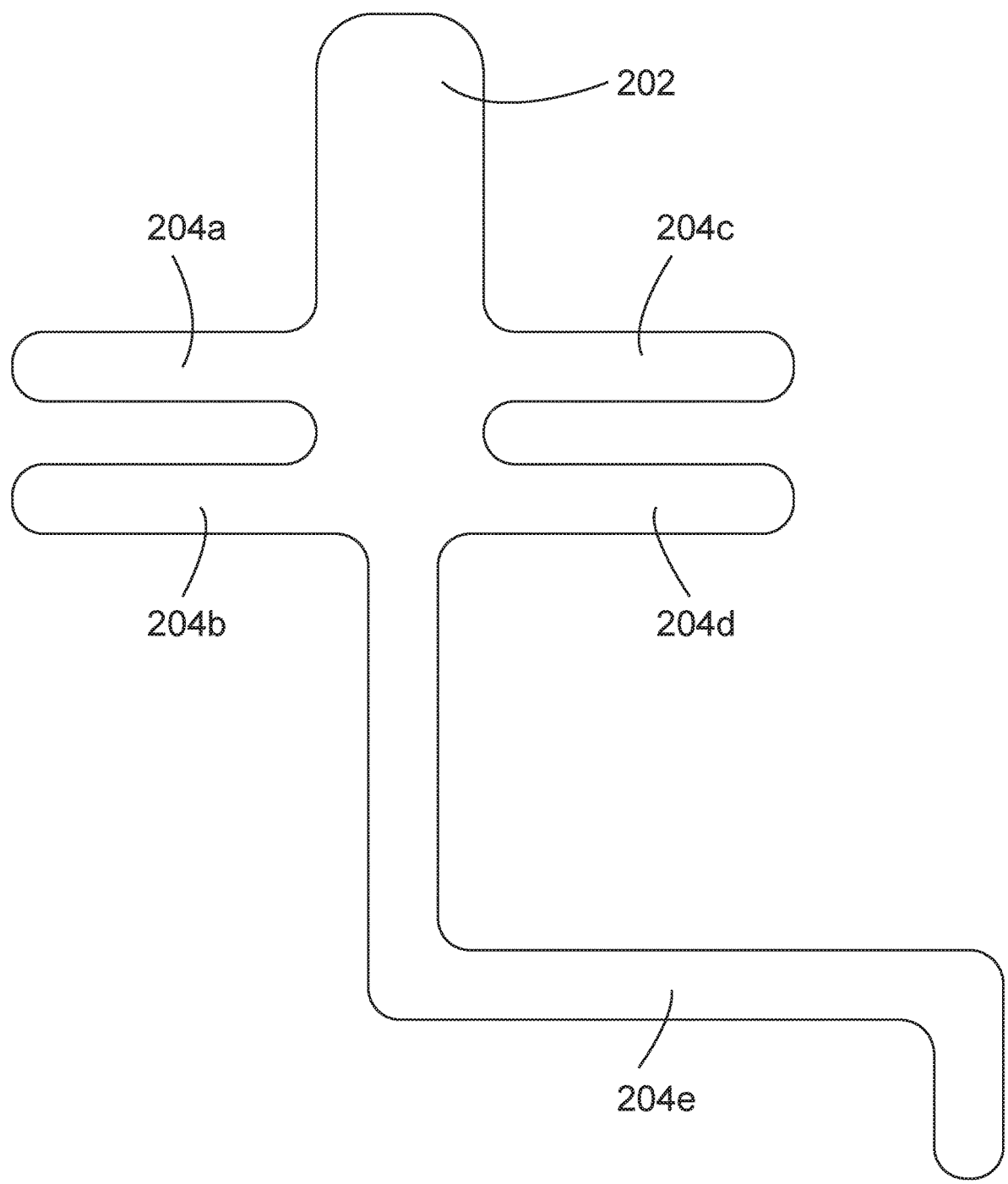
FIGS. 2C-2I show various layers of an example multi-layered lead assembly.

FIG. 2C shows a first anti-static layer 202 which can comprise, for example, an anti-static satin fabric. In some embodiments, the anti-static layer 202 is partially conductive. The anti-static layer 202 is configured to reduce, minimize, or eliminate signal distortions or noise due to environmental static. The extending portions 204a-e of the anti-static layer 202 form portions of the respective extending portions 108a-e of the multi-layered lead assembly 102.

Figure 2D:
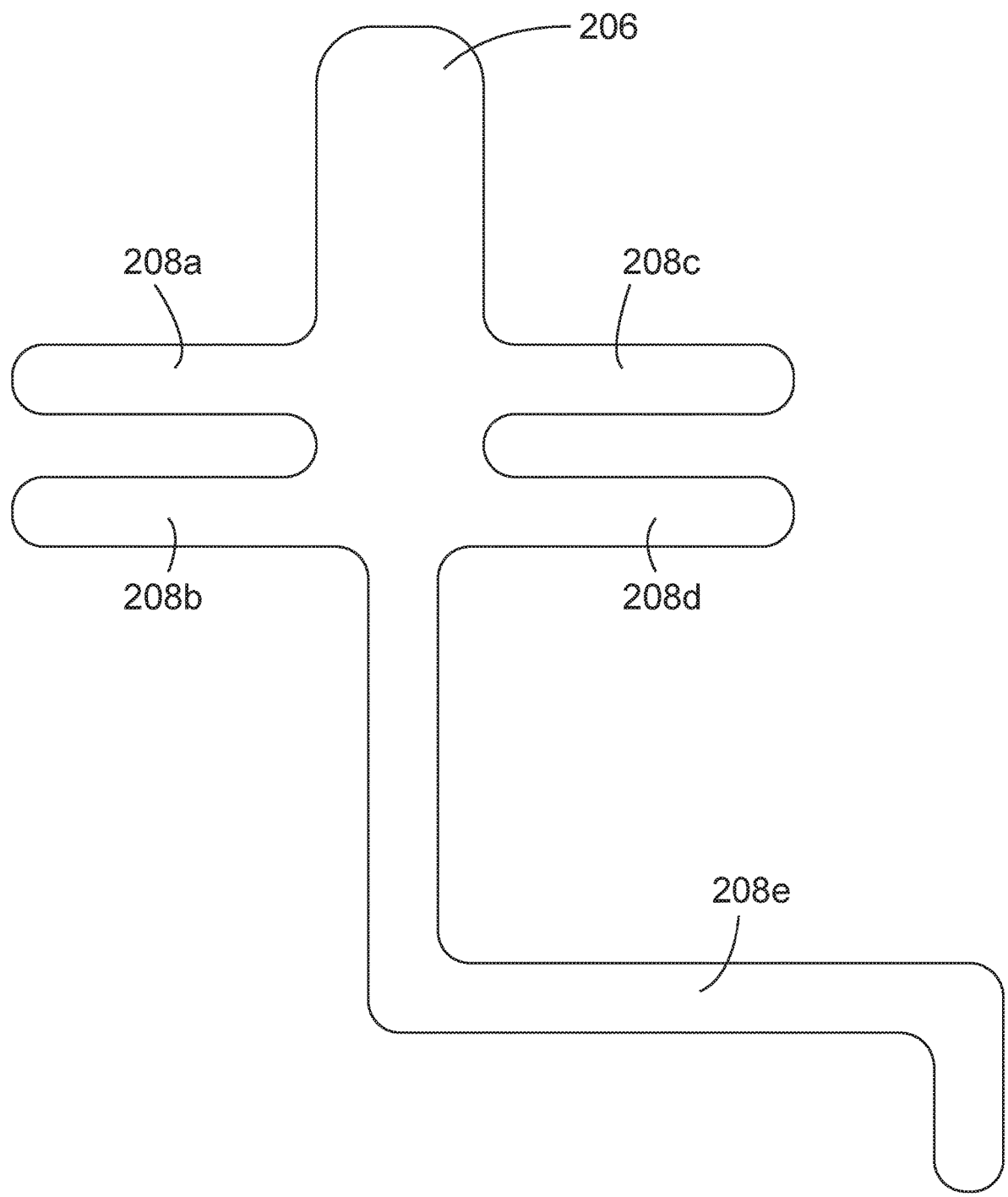

FIG. 2D shows a first insulation layer 206. The insulation layer 206 can comprise a muslin fabric, such as cotton. The insulation layer 206 can help to insulate electrical traces of the multi-layered lead assembly 102 from interference/noise, such as interference due to static electricity. The extending portions 208a-e of the first insulation layer 206 form portions of the respective extending portions 108a-e of the multi-layered lead assembly 102.

Figure 2E:
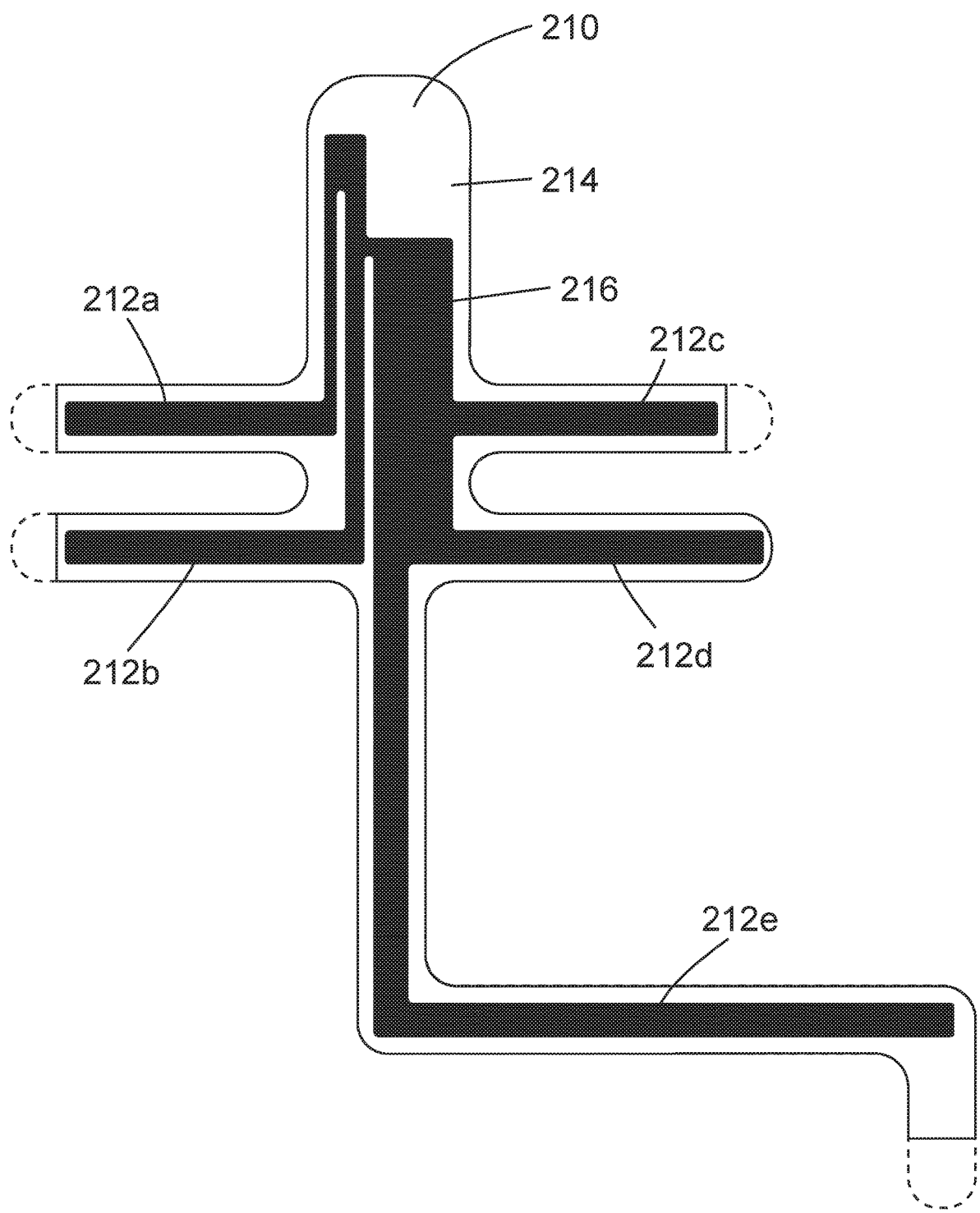

FIG. 2E shows a first shield layer 210. This shield layer comprises muslin fabric 214 (e.g., cotton) integrated with a silver fabric 216 that serves the purpose of reducing or eliminating "cross talk" noise between the various electrical traces (described in greater detail below) in the multi-layered lead assembly 102. The black portions of FIG. 2E show where the silver fabric 216 is included in this shield layer 210 with the white portions 214 showing portions where only muslin fabric 214 is present. In some embodiments the muslin layer 214 extends to the border of the first shield layer 210 to reduce chances of conductive thread touching the silver fabric 216. The extending portions 212a-e of the first shield layer 210 form portions of the respective extending portions 108a-e of the multi-layered lead assembly 102.

Figure 2F:
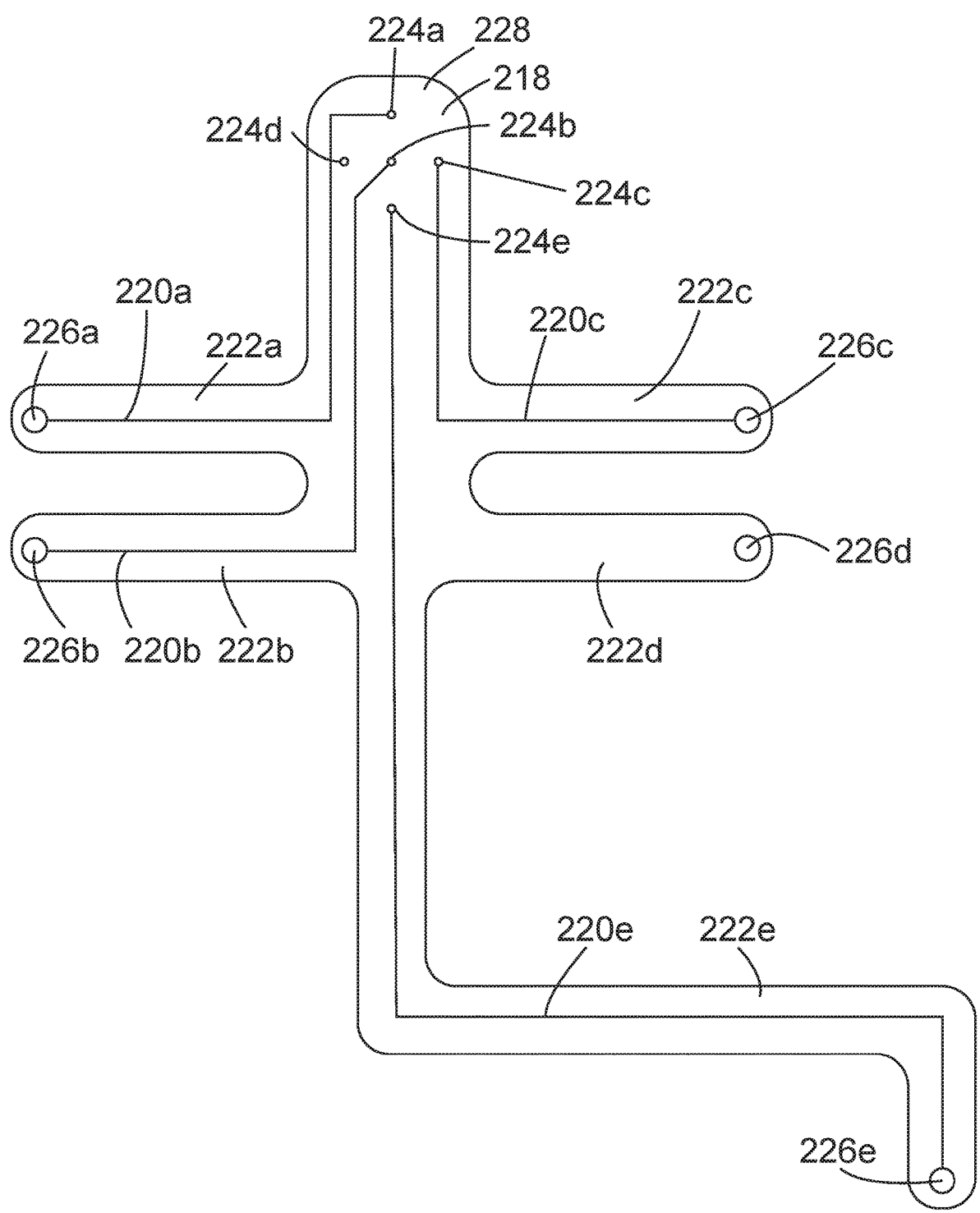

FIG. 2F shows a center layer 218 (also referred to as a trace layer, or lead layer) that includes traces 220a, 220b, 220c, and 220e from the electrical contacts 124a, 124b, 124c, and 124e to the sensor assembly 110. This center layer 218 comprises fabric with conductive thread (or alternatively conductive thread not integrated with other fabrics, or a layer that is substantially composed of conductive thread). The fabric can be, for example, cotton. In some embodiments, the conductive thread has silver woven through it. The conductive thread can connect to electrodes at various points and to the sensor assembly 110 that processes vital sign information sensed at the electrodes (e.g., for the purpose of transmitting the information to an external computing device). Portions of the conductive thread layer can terminate in contact with snap connectors for engaging electrodes of adherent electrode pads and for connecting the conductive thread to the sensor assembly. For example, the traces 220a, 220b, 220c, and 220e can comprise conductive thread and can terminate at respective ends 226a, 226b, 226c, and 226e where the ends 226a, 226b, 226c, and 226e contact electrical contacts 124a, 124b, 124c, and 124e (shown in FIGS. 2A-2B) such that electrical signals received from the skin of a patient wearing the garment 100 are conveyed to the traces 220a, 220b, 220c, and 220e through electrodes (e.g., gel electrodes) affixed to the electrical contacts 124a, 124b, 124c, and 124e located at the ends 226a, 226b, 226c, and 226e of the traces 220a, 220b, 220c, and 220e respectively. For example, portions of the ends 226a, 226b, 226c, and 226e of the traces 220a, 220b, 220c, and 220e can extend through one or more of the layers described infra with respect to FIGS. 2G-2I to contact the respective electrical contacts 124a, 124b, 124c, and 124e. In some implementations, portions of the electrical contacts 124a, 124b, 124c, and 124e can extend through one or more of the layers described infra with respect to FIGS. 2G-2I to contact the respective ends 226a, 226b, 226c, and 226e. The electrical connector 226d can correspond to or otherwise couple with the electrical contact 124d and, in some implementations, in combination with an electrode acts as a ground (or "right leg" electrode). The extending portions 222a-e of the center layer 218 form portions of the respective extending portions 108a-e of the multi-layered lead assembly 102.

In some implementations, the ends 226a, 226b, 226c, and 226e of the traces 220a, 220b, 220c, and 220e are each respectively connected to conductive material (e.g., conductive rubber) that is integrated into the multi-layered lead assembly 102. For example, the conductive material can be integrated into or extend through one or more of the layers described infra with respect to FIGS. 2G-2I.

A top portion 228 of the center layer 218 forms part of the end portion 128 of the multi-layered lead assembly 102. In the example shown, the traces 220a, 220b, 220c, and 220e terminate at the top portion 228 at respective ends 224a, 224b, 224c, and 224e. The ends 224a, 224b, 224c, and 224e each form or otherwise couple to respective snap contacts 112 (e.g., the snap contacts 112 shown in FIGS. 1D and 1F). Thereby, the traces 220a, 220b, 220c, and 220e convey biometric information received from the patient to the sensor assembly 110 via the ends 224a, 224b, 224c, and 224e. The electrical connector 224d can correspond to or otherwise couple with a snap contact 112 to act as a ground. In some implementations, the ends 224a, 224b, 224c, and 224e are arranged to connect to wires of an electrical adapter such as the adapter 114 shown in FIG. 1B-2 that is configured to couple to the sensor assembly 110b to convey the biometric information received from the patient and communicated through the traces 220a, 220b, 220c, and 220e. In some implementations, the ends 224a, 224b, 224c, and 224e can be positioned in different arrangements to adapt to different sensor assembly configurations.

In some embodiments, there is only one layer of the traces layer 218 (fabric with conductive thread layer) depicted in FIG. 2F.

Figure 2G:
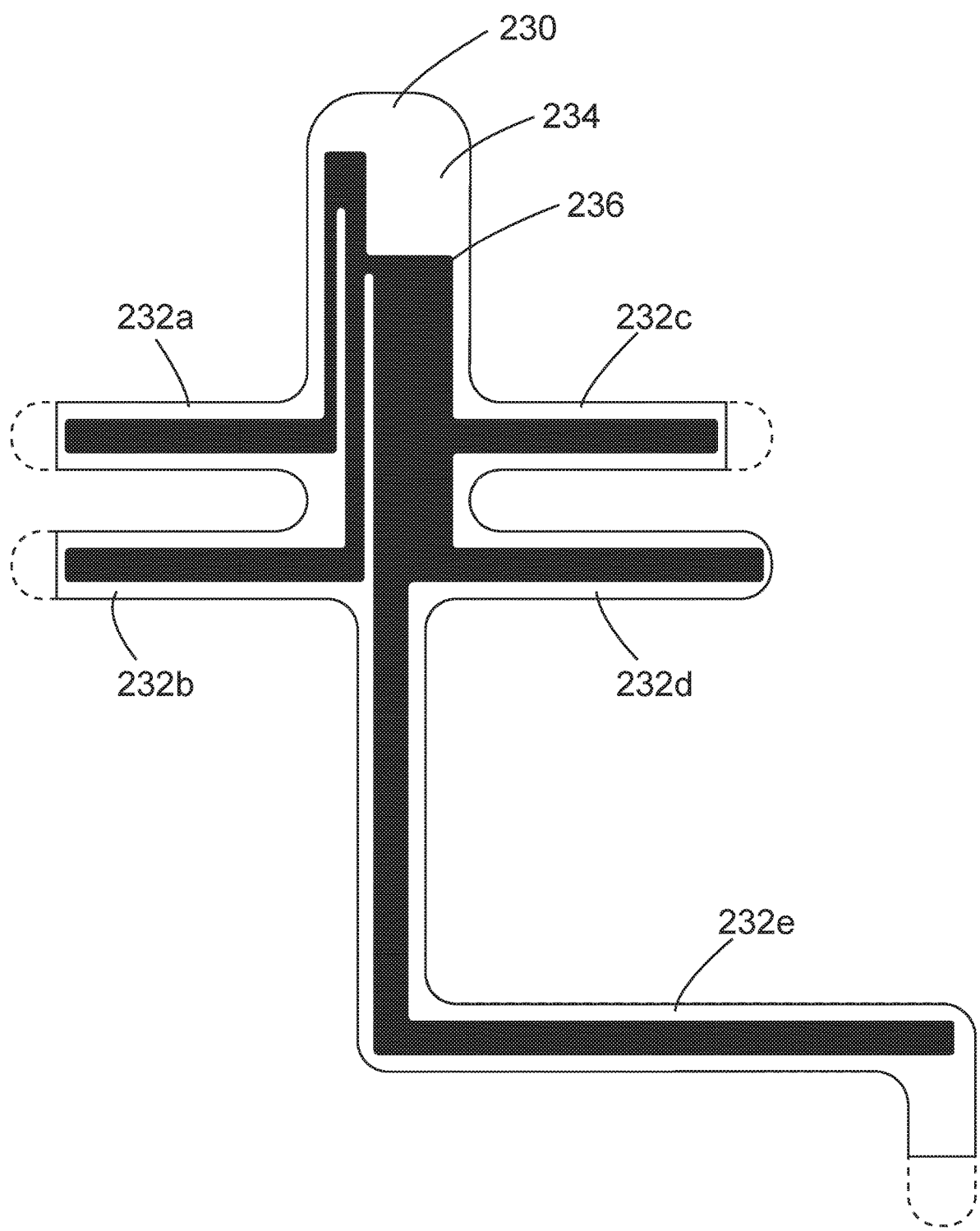

FIG. 2G shows a second shield layer 230. This second shield layer 230 corresponds to the first shield layer 210 depicted in FIG. 2E and comprises muslin fabric 234 (e.g., cotton) integrated with a silver fabric 236 that serves the purpose of reducing or eliminating "cross talk" noise between the various electrical traces (such as electrical traces 220a, 220b, 220c, and 220e) in the multi-layered lead assembly 102. The black portions of FIG. 2G show where the silver fabric 236 is included in the second shield layer 230 with the white portions showing portions where only muslin fabric 234 is present. In some embodiments the muslin layer 214 extends to the border of the second shield layer 230 to reduce chances of conductive thread touching the silver fabric 236. The extending portions 232a-e of the second shield layer 230 form portions of the respective extending portions 108a-e of the multi-layered lead assembly 102.

Figure 2H:
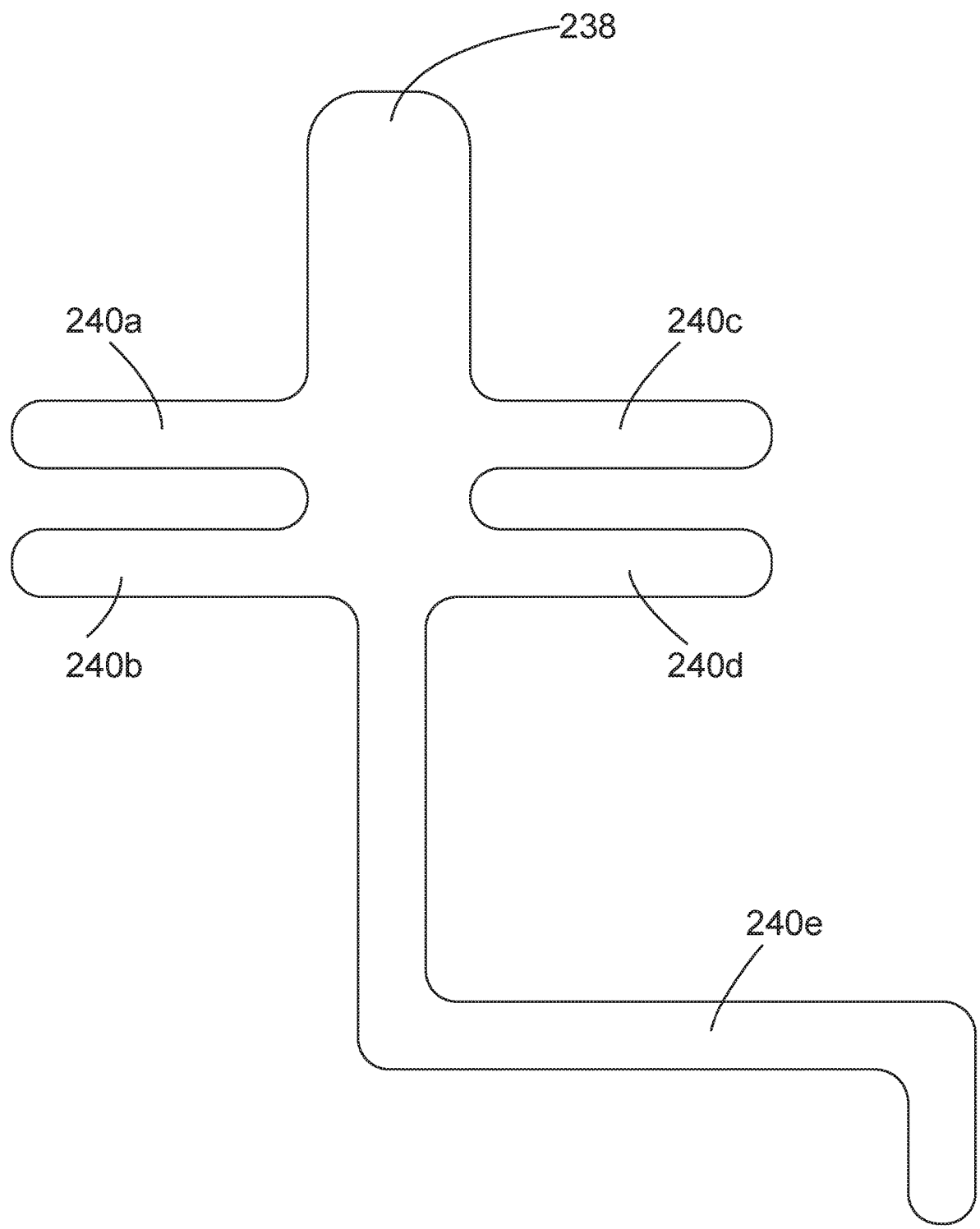

FIG. 2H shows a second insulation layer 238. This second insulation layer 238 corresponds to the first insulation layer 206 depicted in FIG. 2D and can comprise a muslin fabric, such as cotton. The second insulation layer 238 can help to insulate electrical traces (e.g., electrical traces 220a, 220b, 220c, and 220e) of the multi-layered lead assembly 102 from interference/noise, such as interference due to static electricity. The extending portions 240a-e of the second insulation layer 238 form portions of the respective extending portions 108a-e of the multi-layered lead assembly 102.

Figure 2I:
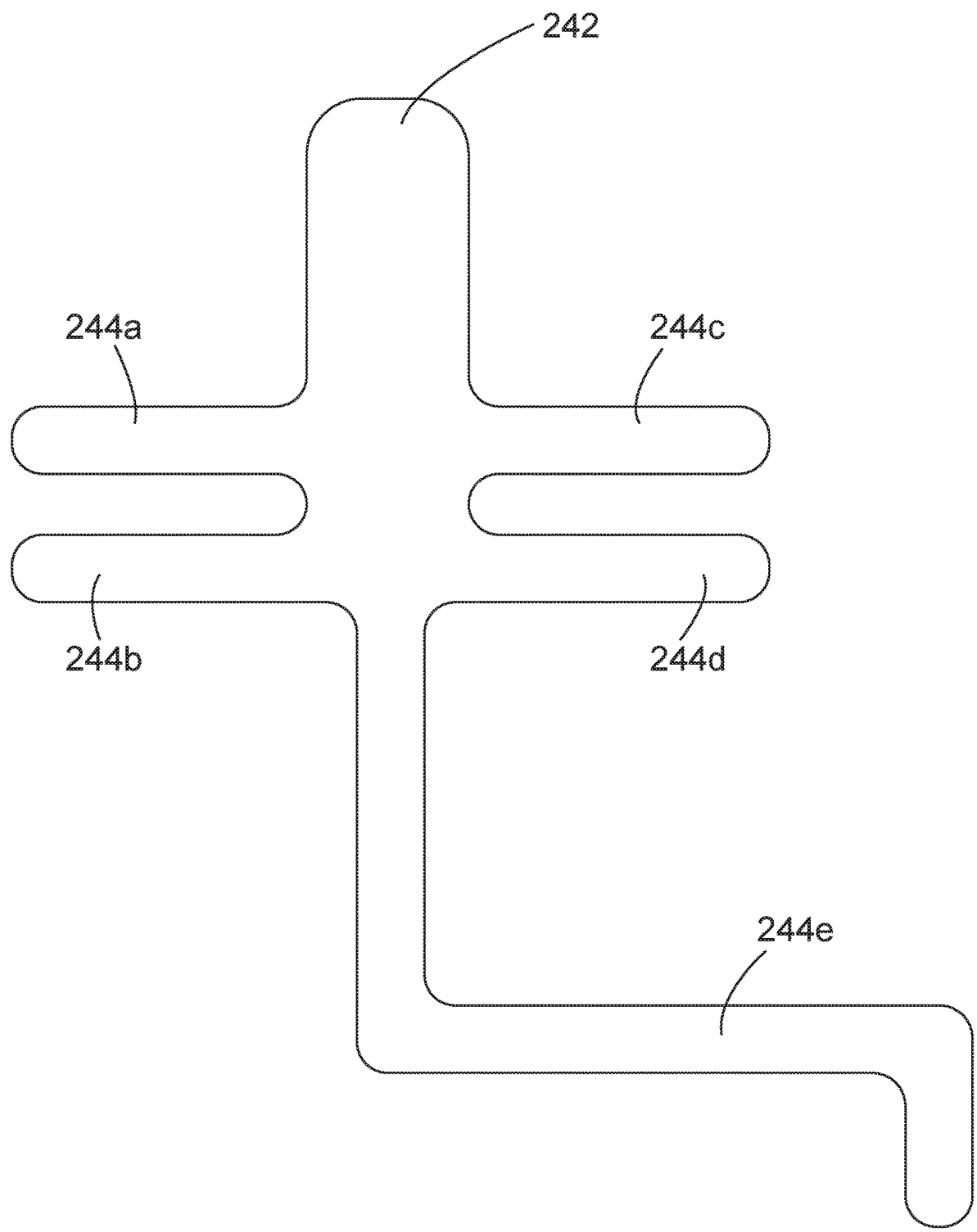

FIG. 2I shows a second anti-static layer 242. This second anti-static layer 242 corresponds to the first anti-static layer 202 depicted in FIG. 2C. The second anti-static layer 242 can be partially conductive. The second anti-static layer 242 is configured to reduce, minimize, or eliminate signal distortions or noise due to environmental static. The extending portions 244a-e of the second anti-static layer 242 form portions of the respective extending portions 108a-e of the multi-layered lead assembly 102.

In some embodiments, the above described layers depicted in FIGS. 2C-2I are arranged in the ordered described. Specifically, the first anti-static layer 202 forms a top layer, followed by the first insulation layer 206, the first shield layer 210, the center layer 218 having traces 220a, 220b, 220c, and 220e then the second shield layer 230, the second insulation layer 238, and finally the second anti-static layer 242. In some embodiments, the multi-layered lead assembly is configured by first sewing conductive thread to the center layer 218, then sewing silver fabric (216, 236) to the first and second shield layers 210 and 230. Next, electrical contact snaps are put through layers 230, 238, and 242 (the fourth to seventh layers shown in FIGS. 2G-2I), all layers are sewn together with a serge edge, and the entire piece is quilted at about 1" squares. Alternatively, quilting can be replaced with two straight stitch lines between traces (e.g., between traces 220a, 220b, 220c, and 220e) to secure larger area from movement. In some embodiments, the multi-layered lead assembly 102 is assembled so as to be machine washable such that the multi-layered lead assembly 102 does not need to be detached from a garment when the garment is washed (only the electrodes and/or sensor assembly 110 need be detached).

In some embodiments, one or more layers are omitted from the multi-layered lead assembly 102. For example, the muslin fabric insulator layers could be omitted. As another example, the anti-static layers could be omitted. As yet another example, the shiled layers could be omitted.

Figure 3A:
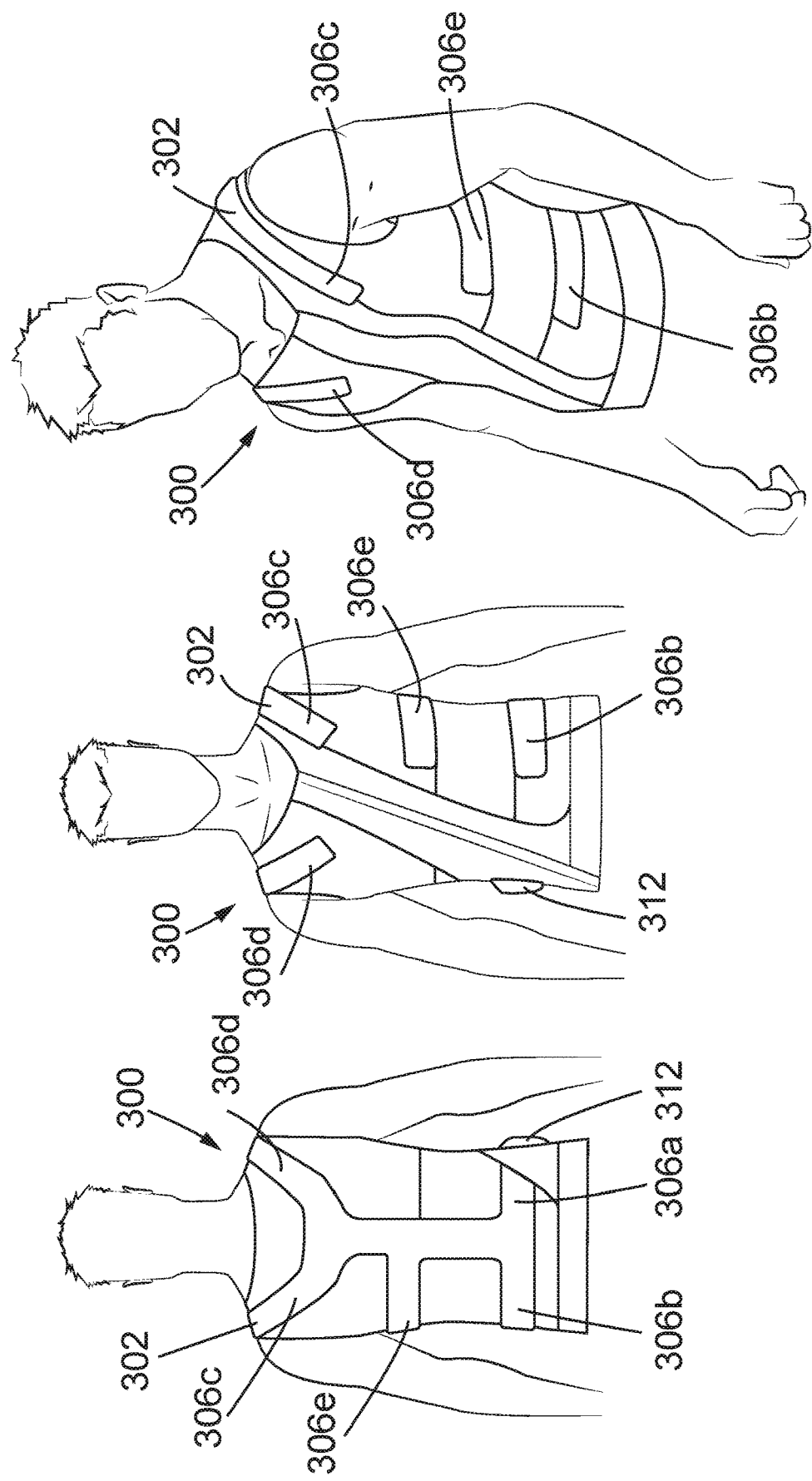
FIGS. 3A-3D show example embodiments of another garment that includes a multi-layered lead assembly configured to contact a sensor assembly and various electrodes.
Figure 3B:
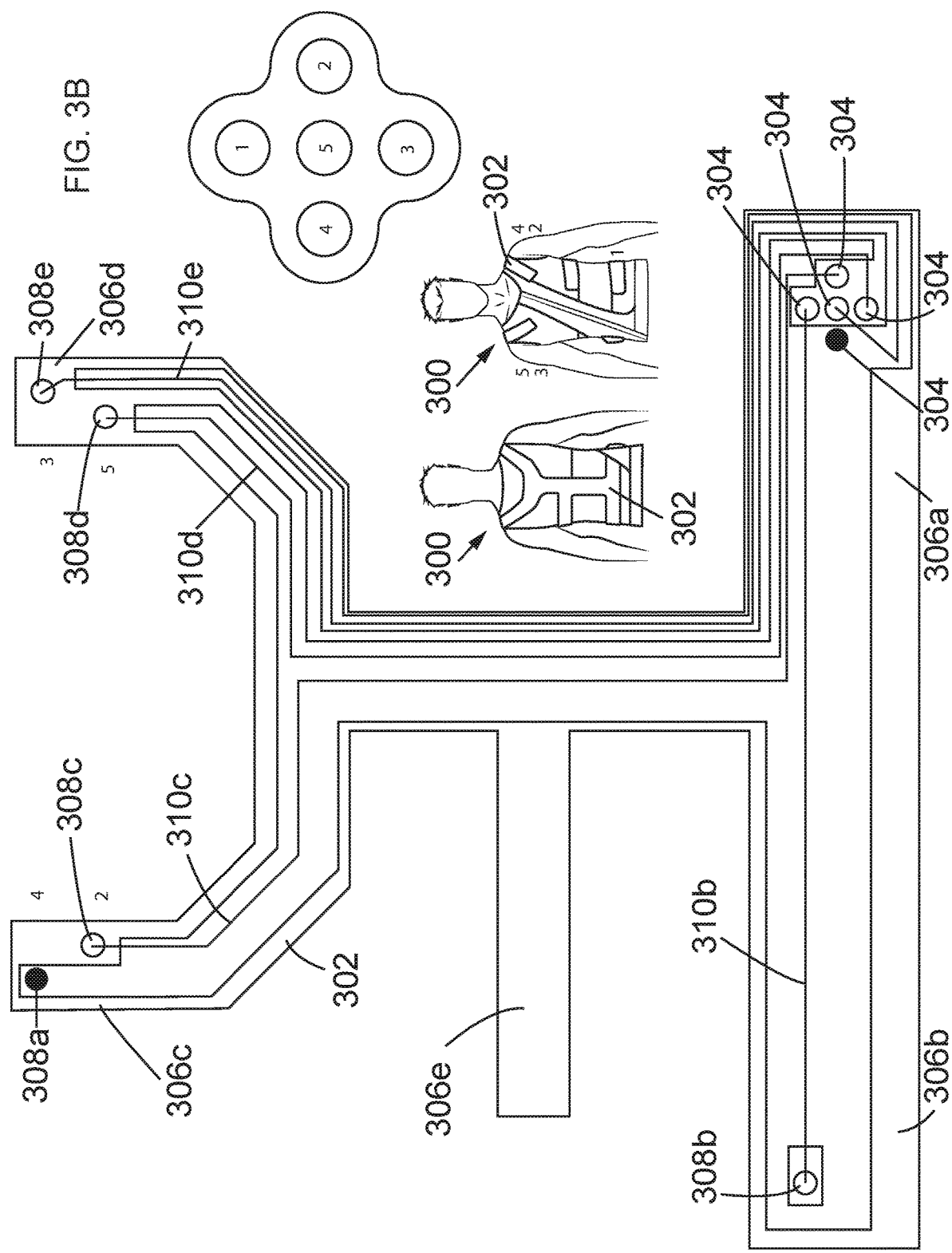

FIGS. 3A-3D show another embodiment of a garment 300 having a multi-layered lead assembly 302. The multi-layered lead assembly 302 can include, for example, the layers shown in FIGS. 2C-2I (and in the order described above) but in a different general shape to conform to the garment 300 shown in FIGS. 3A-3D which has a front zip configuration (or alternatively an overhead configuration without a front or back opening). The position of the multi-layered lead assembly 302 with respect to the garment 300 is shown in FIGS. 3A-3B. Turning to FIG. 3B, the male snaps 304 shown in the bottom right at the end of extending portion 306a are configured to engage female snaps of a sensor assembly such as the type shown in FIGS. 1B-1 and described in greater detail in U.S. patent application Ser. No. 15/019,431 (previously incorporated by reference). Alternatively, the male snaps 304 can be partially or completely replaced by an adapter having a connector, such as the adapter 114 described with respect to FIG. 1B-2 configured for engaging with the sensor assembly 110B of FIG. 1B-2.

Looking to the bottom left of FIG. 3B, this extending portion 306b wraps around to the front of the patient wearing the garment 300 and the female snap 308b can connect to an electrode configured to affix to the skin of the patient and serve as a "left leg" electrode. The female snap 308c located on extending portion 306c can connect to an electrode that is configured to affix to the skin of the patient to serve as a "left arm" electrode. The female snap 308a on extending portion 306c can connect to an electrode configured to affix to the patient's skin to serve as a reference electrode, more commonly with limb leads, the "right leg" electrode (e.g., ground electrode). The female snap 308d on extending portion 306d can connect to an electrode configured to affix to the patient's skin and serve as a "right arm" electrode. The female snap 308e on extending portion 306d can connect to an electrode configured to affix to the patient's skin that is used in a bio-impedance measurement (e.g., serves as the current injector in a bio-impedance measurement in which the right leg electrode is the current collector). The extending portion 306e can help to secure the multi-layered lead assembly 302 within the garment 300 to provide extra support and prevent unwanted motion or bunching of the multi-layered lead assembly 302 when in use.

Electrical traces 310b, 310c, 310d, and 310e of the garment 300 connect the respective female snaps 308b, 308c, 308d, and 308e (and their corresponding electrodes) to respective male snaps 304 for transmitting signals detected at the patient to a sensor assembly.

This configuration of electrodes can be used to collect various vital sign measurements. For example, the left arm and right arm electrodes can be used as a Lead I in an ECG measurement while the right arm and left leg electrodes are used as a Lead II in an ECG measurement. In some implementations, the right leg electrode serves as a ground.

Returning to FIG. 3A, the garment 300 includes a pocket 312 for holding a sensor assembly and reducing movement of the sensor assembly with respect to the garment 300. The extending portion 306a of the multi-layered lead assembly 302 can terminate at or near the pocket 312 such that the sensor assembly can affix to the snaps 304 while positioned within the pocket 312.

Figure 3C:
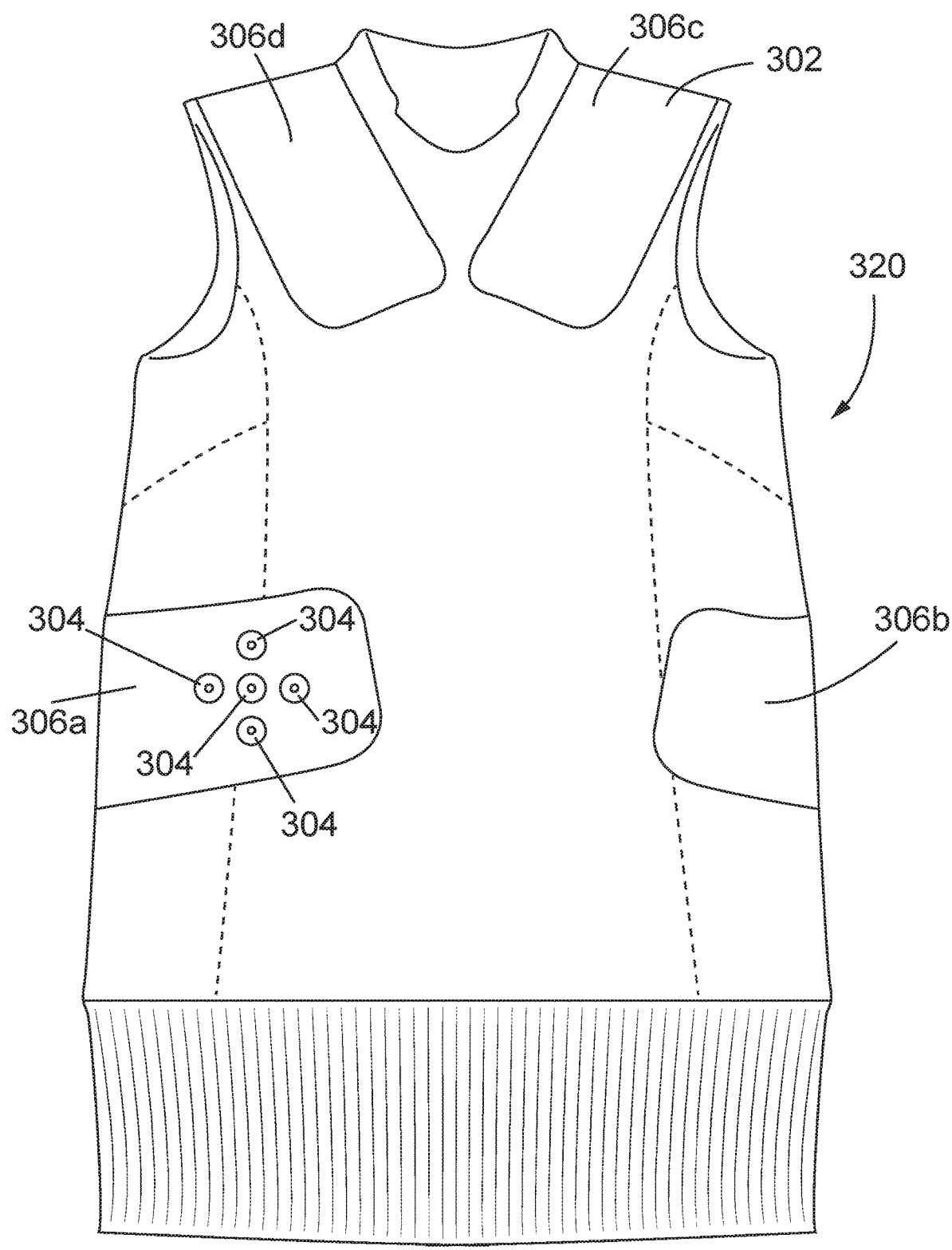
Figure 3D:
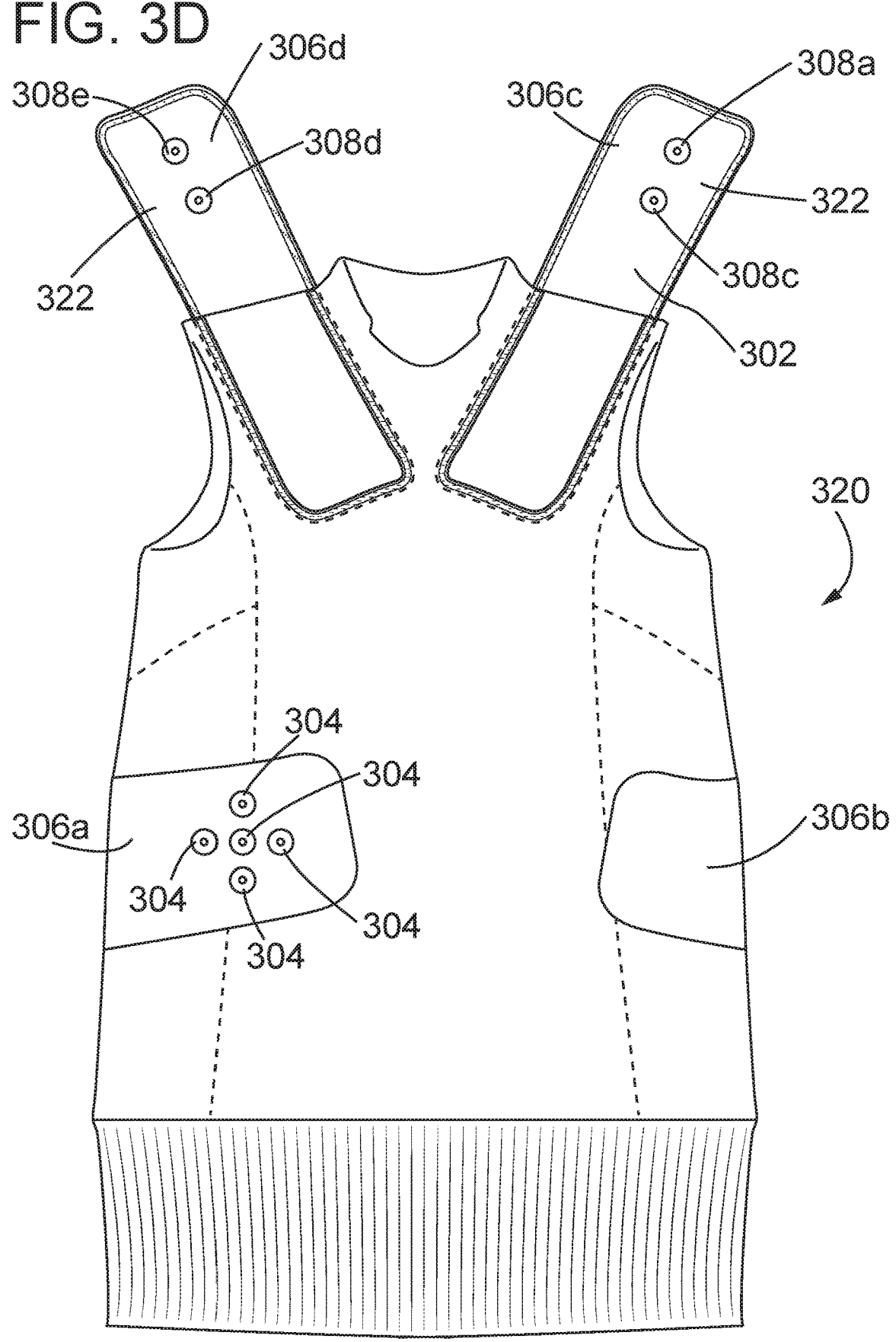

FIGS. 3C-3D show an alternative embodiment of the garment 300 shown in FIG. 3A that uses the same multi-layered lead assembly 302 shown in FIG. 3B except, in this embodiment, with the extending portion 306e omitted. The garment 320 shown in FIGS. 3C-3G is of a pull-over variety rather than having a front zipper. As shown in FIG. 3C, the male contacts 304 for engaging the sensor assembly are located on the front right of the patient when the shirt is being worn. In some embodiments, the garment includes a pocket near this portion to hold the sensor assembly. The extending portions 306a-d wrap around the garment as shown to allow electrical signals received from the patient via electrodes in contact with the patient's skin to be transmitted to the sensor assembly, as described above.

The garment 320 further includes openable flaps 322 near each shoulder for providing access to some of the female contacts (308a, 308c, 308d, and 308e) of the multi-layered lead assembly 302 for engaging electrodes that affix to the patient's chest (the previously described left arm, right arm, right leg, and bio-impedance current injection electrodes). FIG. 3C show the openable flaps 322 in a closed position while FIG. 3D shows the openable flaps 322 in an open position. The flaps can be secured in the closed position by conventional connectors such as hook and loop fasteners (such as the type provided by the Velcro company), buttons, zippers, or other fasteners. As shown in FIG. 3D, when the flaps are in the open position, the female contacts (308a, 308c, 308d, and 308e) of the multi-layered lead assembly 302 can be easily accessed to allow electrodes to be attached to the female contacts (308a, 308c, 308d, and 308e) and properly positioned on the patient's skin. In some implementations, the garment 320 can further include openable flaps at one or both of the extending portions 306a and 306b.

For example, an openable flap at extending portion 306b can allow for easy access of the female contact 308b located on extending portion 306b.

Figure 4A:
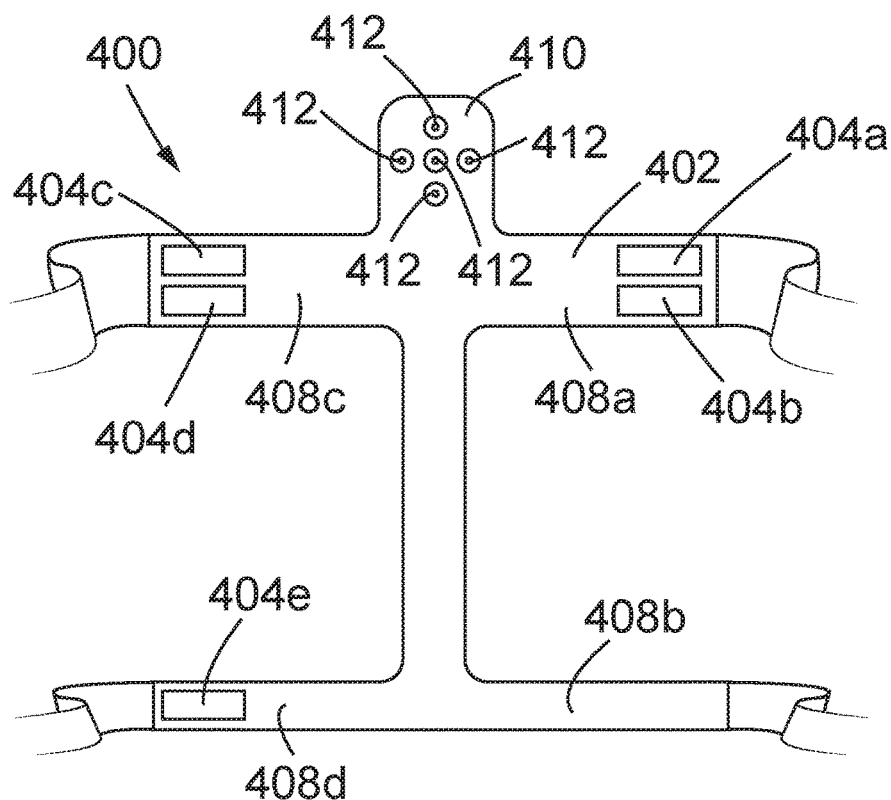
FIGS. 4A-4B shows an example harness that includes conductive rubber electrode contacts and a multilayered lead assembly.
Figure 4B:
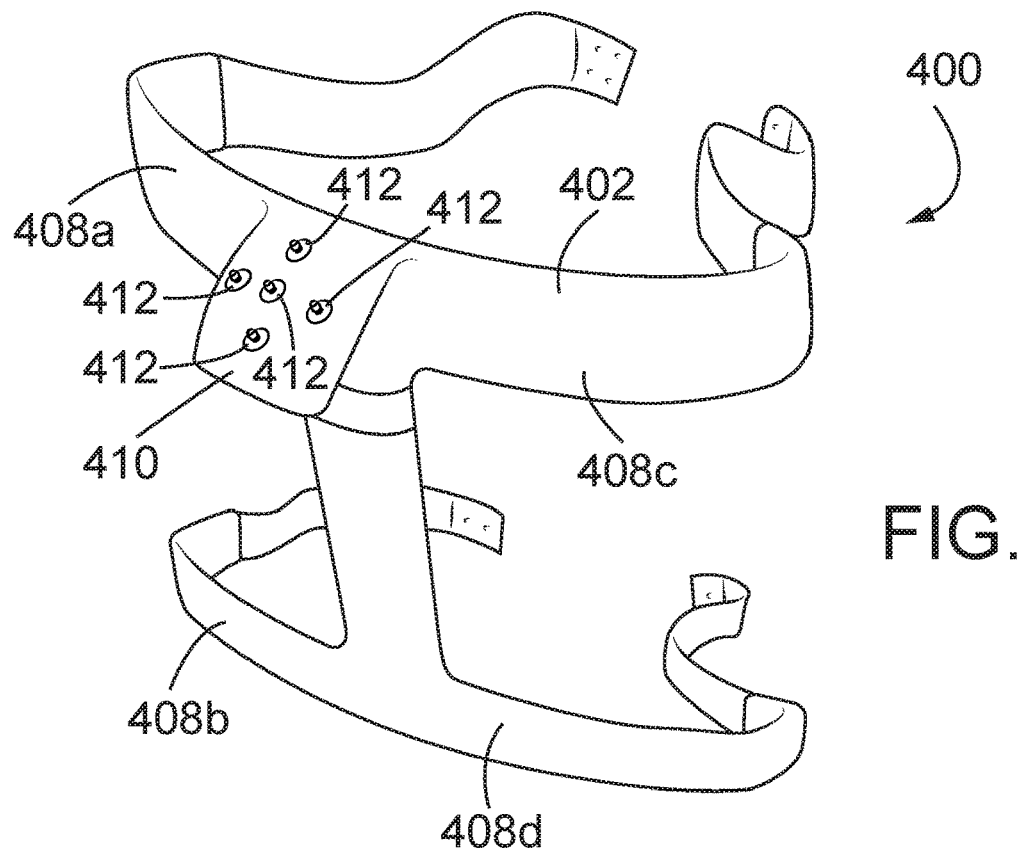

FIGS. 4A-B show a harness 400 that can be worn by a patient either by itself (e.g., under the patient's regular clothing or hospital clothing) or integrated into a garment (such as, for example, the garments 100, 300, or 320). The harness 400 includes a multi-layered lead assembly 402 of the type described above (e.g., having the same layers described with respect to the multi-layered lead assembly 102 above). In the embodiment shown in FIGS. 4A-B, the female electrical contacts of the multi-layered lead assembly 402 have been replaced by conductive material 404 (conductive rubber in the example shown). This conductive material 404 can replace the so called "wet" electrodes by contacting the patient's skin directly. These conductive rubber electrodes can sometimes be referred to as "dry" electrodes. In this configuration the conductive rubber electrodes are in contact with the conductive thread of the center layer (fourth layer described with respect to FIG. 2F) of the multi-layered lead assembly 302.

For example, the conductive material 404c on extending portion 408c can contact the patient's skin to serve as a "left arm" electrode. The conductive material 404d positioned below the conductive material 404c on extending portion 408c can contact the patient's skin to serve as a reference electrode, more commonly with limb leads, the "right leg" (ground) electrode. The upper right conductive material 404a located on the extending portion 408a can connect the patient's skin to serve as a "right arm" electrode, the conductive material 404b immediately below the conductive material 404a on the extending portion 408a can be used in a bio-impedance measurement (e.g., serves as the current injector in a bio-impedance measurement in which the right leg electrode is the current collector). The conductive material 404e located on extending portion 408d can contact the patient's skin to serve as a "left leg" electrode. This configuration of electrodes can be used to collect various vital sign measurements from a patient wearing the harness 400. For example, the left arm and right arm electrodes can be used as a Lead (or vector) I in an ECG measurement while the right arm and left leg electrodes are used as a Lead (or vector) II in an ECG measurement. In some implementations, the right leg electrode serves as a ground.

In some implementations, the harness shown in FIGS. 4A-B must be worn tight to the patient's skin to prevent the electrodes 404a-e from moving with respect to the patient's skin and/or to ensure that sufficient contact with the patient's skin for obtaining accurate measurements is achieved. In some implementations, the lower left lead of the harness 400 can have an L shape such as that shown in FIGS. 2A and 2B.

Figure 5B:
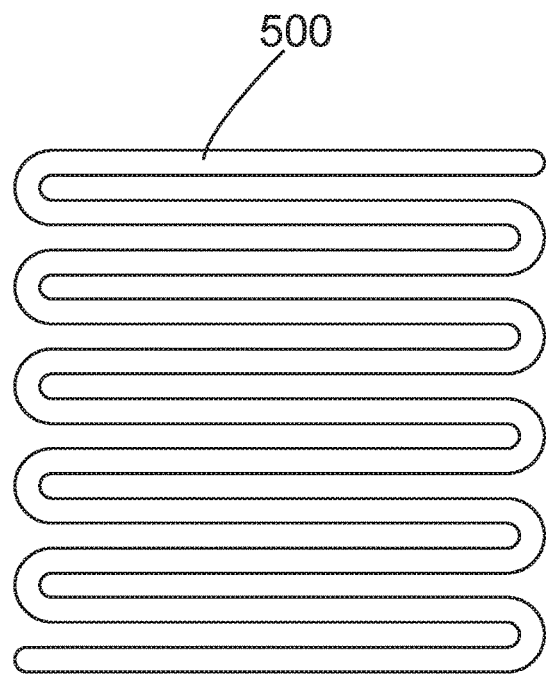
FIG. 5B shows a close up view of the anti-bunching structure of FIG. 5A.
Figure 5A:
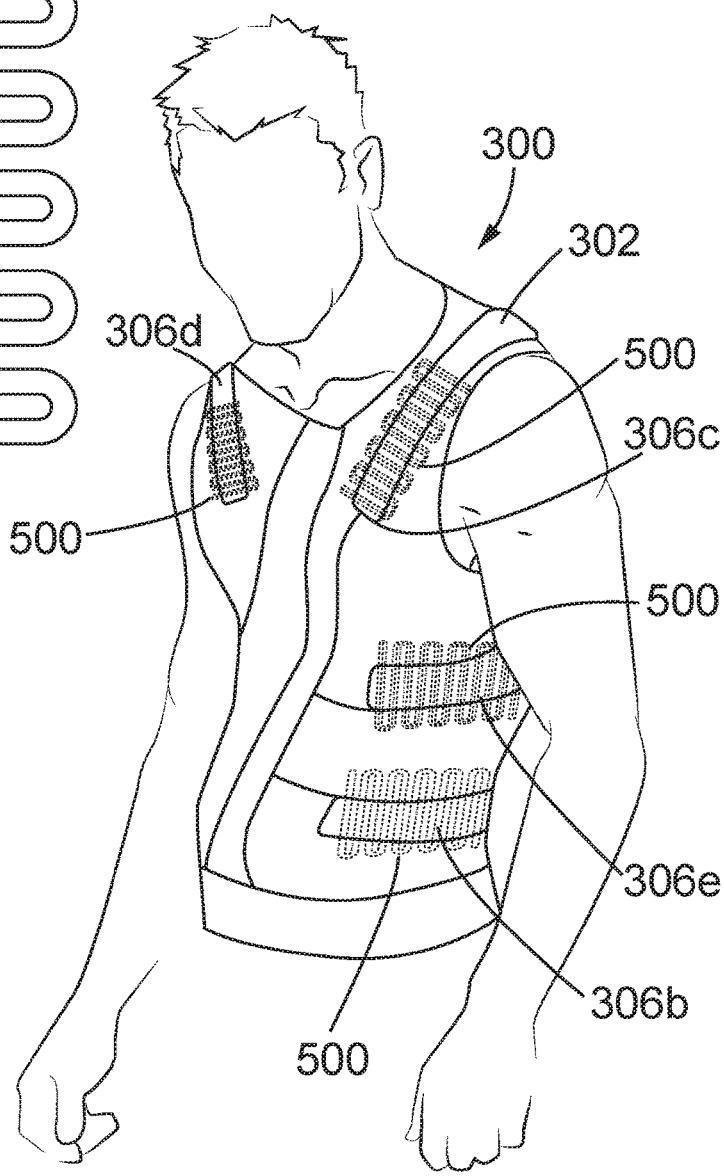
FIG. 5A shows an example embodiment of a garment that includes a multi-layered lead assembly and a plurality of anti-bunching structures.

FIG. 5A shows an alternative embodiment of the garment 300 of FIGS. 3A-3B that includes the multi-layered lead assembly 302 and a plurality of anti-bunching structures 500. FIG. 5B shows a close up view of the anti-bunching structure 500. The anti-bunching structure 500 prevents bunching or malformation of the extending portions 306 of the multi-layered lead assembly 302. This helps to ensure that the electrodes of the multi-layered lead assembly 302 maintain accurate contact with the patient's skin. The anti-bunching structures 500 reduce movement and bunching of the extending portions 306 with respect to the patient and to the garment 300. The anti-bunching structures 500 can be made of a rigid or semi-rigid plastic and be approximately 1/32 inch thick. The shape depicted in FIG. 5B allows for compressing and flexibility of the anti-bunching structure 500 to allow for efficient contouring to a patient's body. For example, the shape of the anti-bunching structure 500 shown in FIG. 5B allows for better contouring to a patient's body than a solid piece of material. The anti-bunching structures 500 therefore allow for contouring to a patient's body while also providing rigid support for the extending portions 306 to reduce movement. The anti-bunching structures 500 can be sewn into the garment 300 over (or under) the locations of the extending portions 306.

The anti-bunching structures 500 are also suitable for use with other embodiments of the garments described above, for example, the garment 100 and the garment 320. For example, the anti-bunching structures 500 can be sewn into the garment 100 over (or under) the extending portions 108 of the garment 100 to provide extra stability and prevent unwanted movement.

Thus, particular embodiments of the subject matter have been described. Other embodiments are within the scope of the following claims. In some cases, the actions recited in the claims can be performed in a different order and still achieve desirable results.

What is claimed is:

1. A multi-layered lead assembly for use with a garment, the multi-layered lead assembly comprising:
   a first anti-static layer;
   a first insulator layer positioned between the first anti-static layer and a first shield layer, wherein the first shield layer comprises muslin fabric integrated with a silver fabric, the muslin fabric of the first shield layer being distinct from fabric of the first insulator layer;
   a center layer having fabric interwoven with conductive thread, such that the conductive thread forms a plurality of electrical traces extending within the center layer, the center layer positioned between the first shield layer and a second shield layer, wherein the second shield layer comprises muslin fabric integrated with a silver fabric;
   a second insulator layer, the second insulator layer being distinct from the muslin fabric of the second shield layer; and
   a second anti-static layer, wherein the second insulator layer, is positioned between the second shield layer and the second anti-static layer; and
   wherein the first anti-static layer, first insulator layer, first shield layer, center layer, second shield layer, second insulator layer, and second anti-static layer are configured to be sewn together to form the multi-layered lead assembly.

2. The multi-layered lead assembly of claim 1, wherein the silver fabric of the first and second shield layers does not extend to the edges of the first and second shield layers.

3. The multi-layered lead assembly of claim 1, wherein the conductive thread of the center layer has silver woven through it.

4. The multi-layered lead assembly of claim 1, wherein the center layer includes four distinct electrical traces formed from the conductive thread such that each of the four electrical traces terminates at a first end configured to electrically couple with a respective electrode for contacting skin of a patient and wherein each of the four electrical traces terminates at a second end configured to electrically couple with a sensor assembly.

5. The multi-layered lead assembly of claim 4, wherein the first end of each electrical trace is configured to electrically couple with the respective electrode via a female snap connector.

6. The multi-layered lead assembly of claim 4, wherein each respective electrode comprises a portion of conductive rubber and the first end of each electrical trace is configured to electrically couple with the respective portion of conductive rubber.

7. The multi-layered lead assembly of claim 4, wherein the second end of each electrical trace is configured to electrically couple with the sensor assembly via a male snap connector.

8. The multi-layered lead assembly of claim 4, wherein the second end of each electrical trace forms at least a portion of an adapter configured to electrically couple with the sensor assembly.

9. The multi-layered lead assembly of claim 1, wherein the first and second anti-static layers comprise satin fabric.

10. The multi-layered lead assembly of claim 1, wherein:
the first and second anti-static layers comprise satin fabric;
the first and second insulator layers comprise muslin fabric; and
the conductive thread of the center layer comprises silver.

11. The multi-layered lead assembly of claim 1, further comprising:
a first extending portion having a first electrical connector for connecting a first electrical trace of the center layer to a first electrode such that the first electrical trace and the first electrode form a left arm type electrode, wherein the first electrical trace terminates at an end opposite the first electrode at a first connector configured to engage a sensor assembly;
a second extending portion having a second electrical connector for connecting a second electrical trace of the center layer to a second electrode such that the second electrical trace and the second electrode form a right arm type electrode, wherein the second electrical trace terminates at an end opposite the second electrode at a second connector configured to engage the sensor assembly; and
a third extending portion having a third electrical connector for connecting a third electrical trace of the center layer to a third electrode such that the third electrical trace and the third electrode form a left leg type electrode, wherein the third electrical trace terminates at an end opposite the third electrode at a third connector configured to engage the sensor assembly.

12. The multi-layered lead assembly of claim 11, further comprising:
a fourth extending portion having a fourth electrical connector for connecting a fourth electrical trace of the center layer to a fourth electrode such that the fourth electrical trace and the fourth electrode form a current injection electrode for injecting current as part of a bio-impedance measurement process, wherein the fourth electrical trace terminates at an end opposite the fourth electrode at a fourth connector configured to engage the sensor assembly.

13. The multi-layered lead assembly of claim 11, wherein the third extending portion is generally L shaped.

14. The multi-layered lead assembly of claim 11, wherein the first, second, and third connectors are male snap connectors.

15. The multi-layered lead assembly of claim 11, wherein the first, second, and third connectors make up at least a part of an adapter having a wire portion and a connector portion, the connector portion configured to engage a corresponding connector portion of the sensor assembly.

16. A garment configured to at least partially cover a torso of a patient, the garment comprising a multi-layered lead assembly permanently affixed to the garment, the multi-layered lead assembly comprising:
a first anti-static layer;
a first insulator layer;
a first shield layer, wherein the first insulator layer is positioned between the first anti-static layer and the first shield layer;
a center layer having fabric interwoven with conductive thread, such that the conductive thread forms a plurality of electrical traces extending within the center layer, the center layer positioned between the first shield layer and a second shield layer;
a second insulator layer, wherein the second insulator layer is positioned on an opposite side of the center layer from the first insulator layer;
a second anti-static layer, wherein the first shield layer, center layer, and second shield layer are configured to be sewn together to form the multi-layered lead assembly;
wherein the multi-layered lead assembly comprises a plurality of extensions, each extension having at least one corresponding electrical connector; and
wherein the garment includes a plurality of openings on a chest portion of the garment, wherein each opening of the plurality of openings is configured to allow access to at least one of the plurality of extensions, and wherein at least one of the plurality of openings is configured to permit at least one of the plurality of extensions to extend through the at least one of the plurality of openings.

17. A garment configured to at least partially cover a torso of a patient, the garment comprising a multi-layered lead assembly for collecting bio-metric signals from a patient, the multi-layered lead assembly comprising:
a first anti-static layer;
a first insulator layer;
a first shield layer comprising muslin fabric integrated with a silver fabric, wherein the first insulator layer is positioned between the first anti-static layer and the first shield layer;
a center layer having fabric interwoven with conductive thread, such that the conductive thread forms a plurality of electrical traces extending within the center layer;
a second shield layer, the second shield layer comprising muslin fabric integrated with a silver fabric, wherein the center layer is positioned between the first shield layer and the second shield layer;
a second insulator layer, wherein the second insulator layer is positioned on an opposite side of the center layer from the first insulator layer;
a second anti-static layer, wherein the second insulator layer is positioned between the second shield layer and the second anti-static layer;
wherein the multi-layered lead assembly comprises a plurality of extensions, each extension having at least one corresponding electrical connector; and
wherein the garment includes a plurality of openings on a chest portion of the garment, wherein each opening of the plurality of openings is configured to allow access to at least one of the plurality of extensions, and wherein at least one of the plurality of openings is configured to permit at least one of the plurality of extensions to extend through the at least one of the plurality of openings.

18. The garment of claim 16 further comprising an anti-bunching structure permanently affixed to the garment at a location of at least one of the extensions.

\* \* \* \* \*